US010566176B2

(12) United States Patent
Oh et al.

(10) Patent No.: US 10,566,176 B2
(45) Date of Patent: Feb. 18, 2020

(54) MICROWAVE PROBE, PLASMA MONITORING SYSTEM INCLUDING THE MICROWAVE PROBE, AND METHOD FOR FABRICATING SEMICONDUCTOR DEVICE USING THE SYSTEM

(71) Applicant: Samsung Electronics Co., Ltd., Suwon-si (KR)

(72) Inventors: Se-jin Oh, Hwaseong-si (KR); Woong Ko, Osan-si (KR); Vasily Pashkovskiy, Osan-si (KR); Doug-yong Sung, Seoul (KR); Ki-ho Hwang, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 394 days.

(21) Appl. No.: 15/426,672

(22) Filed: Feb. 7, 2017

(65) Prior Publication Data

US 2017/0148613 A1    May 25, 2017

Related U.S. Application Data

(63) Continuation of application No. 15/163,876, filed on May 25, 2016, now Pat. No. 9,601,397.

(30) Foreign Application Priority Data

Sep. 3, 2015   (KR) .................. 10-2015-0124942

(51) Int. Cl.
*H01J 37/32* (2006.01)
*H01L 21/66* (2006.01)
(Continued)

(52) U.S. Cl.
CPC ........ *H01J 37/32935* (2013.01); *G01N 22/00* (2013.01); *H01J 37/32082* (2013.01);
(Continued)

(58) Field of Classification Search
CPC ... H01L 22/26; H01L 21/263; H01L 21/3065; H01L 21/67253; G01N 22/00; H01J 37/32082; H01J 37/32935; H01R 9/05
See application file for complete search history.

(56) References Cited

U.S. PATENT DOCUMENTS 6,060,329 A     5/2000  Kamata et al.
6,356,097 B1 *  3/2002  Loewenhardt ........ B24B 37/013
                                                    257/E21.528
(Continued)

FOREIGN PATENT DOCUMENTS

JP    2005-203124    7/2005
JP    2005-235677    9/2005
(Continued)

OTHER PUBLICATIONS

Garvin et al. "Advances in broadband radio-frequency sensing for real-time control of plasma-based semiconductor processing" *Journal of Vacuum Science & Technology A* 17(4):1377-1383 (1999).
(Continued)

*Primary Examiner* — Yuechuan Yu
(74) *Attorney, Agent, or Firm* — Myers Bigel, P.A.

(57) ABSTRACT

Disclosed herein are a microwave probe capable of precisely detecting a plasma state in a plasma process, a plasma monitoring system including the probe, and a method of fabricating a semiconductor device using the system. The microwave probe includes a body extending in one direction and a head which is connected to one end of the body and has a flat plate shape. In addition, in the plasma process, the microwave probe is non-invasively coupled to a chamber such that a surface of the head contacts an outer surface of a viewport of the chamber, and the microwave probe applies a microwave into the chamber through the head and receives signals generated inside the chamber through the head.

19 Claims, 32 Drawing Sheets

(51) Int. Cl.
*H01L 21/263* (2006.01)
*G01N 22/00* (2006.01)
*H01L 21/3065* (2006.01)
*H01L 21/67* (2006.01)
*H01R 9/05* (2006.01)

(52) U.S. Cl.
CPC ........ *H01L 21/263* (2013.01); *H01L 21/3065* (2013.01); *H01L 21/67253* (2013.01); *H01L 22/26* (2013.01); *H01R 9/05* (2013.01)

(56) References Cited

U.S. PATENT DOCUMENTS

| | | |
|---|---|---|
| 6,646,224 B2 | 11/2003 | Ishii et al. |
| 6,741,944 B1 | 5/2004 | Verdeyen et al. |
| 6,744,211 B2 | 6/2004 | Sugai et al. |
| 6,861,844 B1 | 3/2005 | Verdeyen et al. |
| 6,902,646 B2 | 6/2005 | Mahoney et al. |
| 7,048,837 B2 | 5/2006 | Somekh et al. |
| 7,655,110 B2 | 2/2010 | Yamazawa |
| 2001/0019271 A1 | 9/2001 | Scott et al. |
| 2004/0184028 A1* | 9/2004 | Fink .................. H01J 37/32862 356/72 |
| 2005/0009347 A1* | 1/2005 | Matsumoto ............ G01N 21/68 438/689 |
| 2005/0188922 A1* | 9/2005 | Ishibashi ........... H01J 37/32935 118/723 I |
| 2006/0043063 A1* | 3/2006 | Mahoney .................. C23F 4/00 216/61 |
| 2007/0075036 A1 | 4/2007 | Moroz |
| 2010/0271040 A1* | 10/2010 | Jafarian-Tehrani ......................... G01R 31/026 324/537 |
| 2010/0298738 A1 | 11/2010 | Felts et al. |
| 2011/0109530 A1 | 5/2011 | Nonomura |
| 2012/0084046 A1 | 4/2012 | Boris et al. |

FOREIGN PATENT DOCUMENTS

| | | |
|---|---|---|
| JP | 4418661 | 12/2009 |
| JP | 2010-277695 | 12/2010 |
| JP | 5136514 | 11/2012 |
| JP | 2014-086129 | 5/2014 |
| KR | 10-2008-0006750 | 1/2008 |
| KR | 10-0978556 | 8/2010 |
| KR | 10-2011-0042430 | 4/2011 |
| KR | 10-1325777 | 10/2013 |

OTHER PUBLICATIONS

Klimecky et al. "Compensation for transient chamber wall condition using real-time plasma density feedback control in an inductively coupled plasma etcher" *Journal of Vacuum Science & Technology A* 21(3):706-717 (2003).

Kokura et al. "Plasma Absorption Probe for Measuring Electron Density in an Environment Soiled with Processing Plasmas" *Japanese Journal of Applied Physics* 38:5262-5266 (1999).

Lapke et al. "The multipole resonance probe: A concept for simultaneous determination of plasma density, electron temperature, and collision rate in low-pressure plasmas" *Applied Physics Letters* 93:052501 (2008).

* cited by examiner (a)

(b)

(c)

(d)

(e)

(f)

MICROWAVE PROBE, PLASMA MONITORING SYSTEM INCLUDING THE MICROWAVE PROBE, AND METHOD FOR FABRICATING SEMICONDUCTOR DEVICE USING THE SYSTEM

CROSS-REFERENCE TO RELATED APPLICATION

This application is a continuation of U.S. patent application Ser. No. 15/163,876, filed May 25, 2016 which application claims the benefit of Korean Patent Application No. 10-2015-0124942, filed on Sep. 3, 2015, the disclosures of which are incorporated by reference herein in their entireties.

BACKGROUND

The inventive concept relates to an apparatus and a method for fabricating a semiconductor device, and more particularly, to an apparatus for monitoring a plasma state in a plasma process, and a method for fabricating a semiconductor device using the apparatus.

Plasma is being widely used for processes of manufacturing semiconductors, plasma display panels (PDPs), liquid crystal displays (LCDs), solar cells, and the like. Representative plasma processes include dry etching, plasma enhanced chemical vapor deposition (PECVD), sputtering, ashing, and the like. Generally, capacitively coupled plasma (CCP), inductively coupled plasma (ICP), helicon plasma, microwave plasma, and the like are being used. It is known that plasma processes are directly associated with plasma parameters (for example, an electron density, an electron temperature, an ion flux, and ion energy), and that, in particular, an electron density is closely related to throughput. Therefore, a plasma source having a high electron density is being actively developed.

SUMMARY

The inventive concept provides a microwave probe capable of precisely detecting a plasma state in a plasma process, a plasma monitoring system including the probe, and a method of fabricating a semiconductor device using the system.

According to an aspect of the inventive concept, there is provided a method of fabricating a semiconductor device, which includes: non-invasively coupling a microwave probe to a viewport of a chamber for a plasma process; arranging a wafer inside the chamber; generating plasma by injecting a process gas into the chamber and applying RF power to the chamber; applying a microwave into the chamber through the microwave probe, and receiving signals generated inside the chamber through the microwave probe; and detecting a resonant frequency among the received signals, and analyzing a plasma state inside the chamber based on the resonant frequency, wherein the microwave probe includes a body and a head at one end of the body, and applies the microwave and receives the signals through the head contacting an outer surface of the viewport.

According to another aspect of the inventive concept, there is provided a method of fabricating a semiconductor device, which includes: generating plasma by injecting a process gas into a chamber in which a wafer is arranged and by applying RF power to the chamber; applying a microwave into the chamber and receiving signals generated inside the chamber, through a microwave probe non-invasively coupled to a viewport of the chamber, the microwave probe including a body and a head at one end of the body; and detecting a resonant frequency among the received signals, and analyzing a plasma state inside the chamber based on the resonant frequency.

According to a further aspect of the inventive concept, there is provided a microwave probe which includes: a body extending in one direction; and a head which is connected to one end of the body and has a flat plate structure, wherein in a plasma process, the microwave probe is configured to be non-invasively coupled to a chamber such that a surface of the head contacts an outer surface of a viewport of the chamber, and configured to apply a microwave into the chamber and to receive signals generated inside the chamber through the head.

According to yet another aspect of the inventive concept, there is provided a plasma monitoring system which includes: a chamber for a plasma process; an RF power supply for generating plasma inside the chamber; a microwave probe configured to be non-invasively coupled to a viewport included in the chamber, the microwave probe including a body and a head at one end of the body; and a network analyzer configured to be electrically connected to the microwave probe.

According to yet another aspect of the inventive concept, there is provided a method of fabricating a semiconductor device. The method includes: non-invasively coupling a microwave probe to a viewport held in an outer wall of a chamber for a plasma process; generating plasma by injecting a process gas into the chamber and applying RF power to the chamber; applying a microwave into the chamber through the microwave probe; receiving signals generated inside the chamber through the microwave probe; detecting a resonant frequency among the received signals; and analyzing a plasma state inside the chamber based on the resonant frequency including determining an electron density of the plasma based on the resonant frequency. The microwave probe includes a body and a head at a first end of the body, and the applying of the microwave and the receiving of the signals are performed through the head which contacts an outer surface of the viewport during the non-invasively coupling the microwave probe to the viewport.

According to the inventive concept, in a plasma process, the microwave probe is non-invasively coupled to the viewport of the chamber, and thus can be advantageously used for monitoring a plasma state inside the chamber. For example, since the microwave probe is non-invasively coupled to an outside of the chamber, the microwave probe itself does not affect a plasma state inside the chamber. In addition, using the non-invasive microwave probe, a microwave is applied, and signals inside the chamber are received, whereby the plasma state inside the chamber can be accurately detected and monitored.

According to the inventive concept, the plasma monitoring system includes the microwave probe non-invasively coupled to the viewport of the chamber, whereby the plasma state inside the chamber can be accurately detected without an influence on the plasma state inside the chamber. In addition, the plasma monitoring system precisely monitors whether there is a problem in the plasma state by calculating an electron density based on the measured resonant frequency, and controls process conditions of a plasma process, thereby optimizing the plasma process.

BRIEF DESCRIPTION OF THE DRAWINGS

Example embodiments of the inventive concept will be more clearly understood from the following detailed description taken in conjunction with the accompanying drawings in which.

DETAILED DESCRIPTION OF THE EMBODIMENTS

Figure 1A:
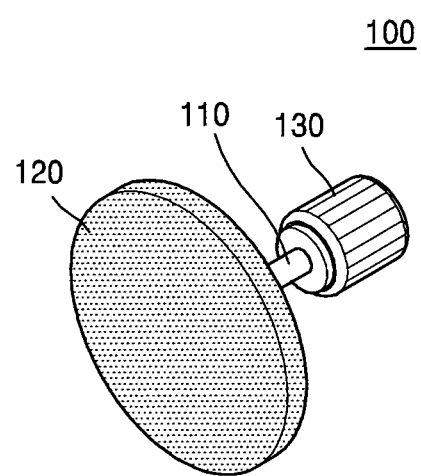
FIGS. 1A and 1B are a perspective view and a side view of a microwave probe according to an example embodiment of the inventive concept.

Hereinafter, example embodiments of the inventive concept will be described in detail with reference to the accompanying drawings. It should be understood that the example embodiments are provided for complete disclosure and thorough understanding of the inventive concept by those of ordinary skill in the art, and that the inventive concept is not limited to the following embodiments and may be embodied in different ways.

As used herein, the term "and/or" includes any and all combinations of one or more of the associated listed items. Expressions such as "at least one of," when preceding a list of elements, modify the entire list of elements and do not modify the individual elements of the list.

It will be understood that when a component is referred to as being connected to another component, the component may be directly connected to the other component, or a third component may also be interposed therebetween. Similarly, when a component is referred to as being placed on another component, the component may be directly placed on the other component, or a third component may also be interposed therebetween. In the drawings, the sizes or structures of components may be exaggerated for clarity, and portions not essential to the description may be omitted for clarity. Like components will be denoted by like reference numerals throughout the specification. In addition, the terminology used herein is only for the purpose of describing specific embodiments of the inventive concept and is not intended to limit the inventive concept.

Figure 1B:
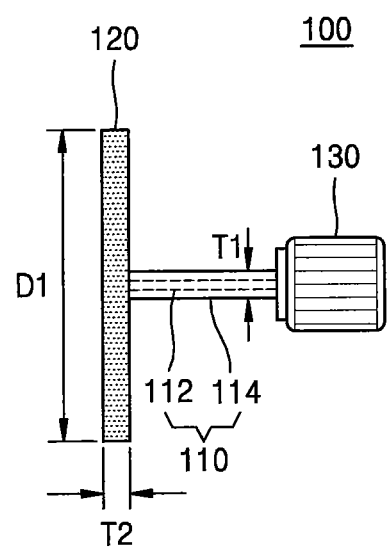

FIGS. 1A and 1B are a perspective view and a side view of a microwave probe according to an example embodiment of the inventive concept.

Referring to FIGS. 1A and 1B, a microwave probe 100 according to the present example embodiment may include a body 110, a head 120, and a connector 130.

The body 110 may include a metal layer 112 and an insulation covering layer 114 surrounding the metal layer 112. The metal layer 112 may include, for example, a metal having good electrical conductivity, such as copper (Cu), aluminum (Al), and the like. The metal layer 112 may be flexible. However, in some cases, flexibility of the metal layer 112 may be suppressed due to an increase in hardness or thickness of the metal layer 112. The metal layer 112 may have a pillar or line shape extending in one direction. The metal layer 112 may have a thickness of about 1 mm and a length of a few centimeters. Of course, the thickness and length of the metal layer 112 are not limited thereto. For reference, the thickness of the metal layer 112 may refer to a diameter when the metal layer 112 has a circular pillar shape, and may refer to a length of a thinner side when the metal layer 112 has a rectangular or quadrangular pillar shape. In some embodiments, the metal layer 112 is a rod.

The insulation covering layer 114 may serve to protect the metal layer 112 and to insulate the metal layer 112 from other conductive materials external to the metal layer 112. For example, as shown in FIGS. 2A to 2D, when a microwave probe 100a includes a conductive ground cover 140, the insulation covering layer 114 may serve to insulate the metal layer 112 and the ground cover 140 from each other. The insulation covering layer 114 may include, for example, cotton, natural rubber, synthetic rubber, a synthetic resin (or plastic), ceramic, or the like.

The insulation covering layer 114 may have a cylindrical tube shape surrounding the metal layer 112. Of course, the shape of the insulation covering layer 114 is not limited thereto. The body 110 including the insulation covering layer 114 may have a first thickness T1 of, for example, 10 mm or less. However, the thickness of the body 110 is not limited thereto. The insulation covering layer 114 may be flexible in conjunction with the metal layer 112. Thus, the body 110 as a whole may be flexible. When flexibility of the metal layer 112 is suppressed, flexibility of the insulation covering layer 114 may also be suppressed, and thus, the insulation covering layer 114 may include a high-hardness plastic or ceramic.

The body 110 may be formed in the same or similar structure as cables used for RF signal transfer. For example, the body 110 may include various RF cables such as RG 58, RG 316, RG 400, RG 402, RG 405, SF/SR 085, SF/SR 141, LMR 200 cables, and the like. In some cases, the insulation covering layer 114 may not be formed in or on the body 110. In other words, the body 110 may include only the metal layer 112, and an outer surface of the metal layer 112 may be exposed to the outside of the metal layer 112. Specific shapes of the body 110 will be described below in more detail with reference to FIG. 6.

The head 120 may be coupled to one end of the body 110, and may have a flat plate structure. For example, the head 120 may have a circular flat plate structure such as a disk. Of course, the structure of the head 120 is not limited thereto. The head 120 may include a metal having good conductivity, such as Cu, Al, and the like, similar to the metal layer 112. For example, the head 120 of the microwave probe 100 may include Cu.

The head 120 may have a different area according to sizes of a viewport (see the reference numeral 220 in FIGS. 8A and 8B) mounted on a chamber. For example, when the head 120 is formed in a circular flat plate structure, the head 120 may have a first diameter D1 of 75% or 80% or more of a diameter of the viewport. For example, when the viewport has a diameter of 5 cm, the head 120 may have a first diameter D1 of 4 cm or more. Of course, the area or diameter of the head 120 is not limited to the numerical values set forth above. For example, the head 120 may have an area that is less than an area corresponding to 75% of the diameter of the viewport, or in some cases, may have an area that is greater than the area of the viewport. In addition, the head 120 may have a second thickness T2 of 10 mm or less. However, the thickness of the head 120 is not limited thereto.

The head 120 may be electrically connected to the metal layer of the body 110. The head 120 may apply a microwave, which is transferred from the outside of the microwave probe 100 through the metal layer 112, into the chamber (see the reference numeral 200 in FIG. 11 or 15). In addition, the head 120 may receive signals generated inside the chamber and transfer the signals to the outside of the microwave probe 100 through the metal layer 112.

To improve the functionality of the head 120 for applying a microwave and/or receiving signals, the head 120 may contact the viewport of the chamber. For example, when the microwave probe 100 is coupled to the viewport of the chamber in a plasma process, the microwave probe 100 may be coupled to the viewport such that a surface of the head 120 contacts an outer surface of the viewport. In addition, to improve the functionality set forth above, various patterns may be formed on the surface of the head 120 contacting the viewport. The structure of the head 120, and the patterns formed on the surface of the head 120 will be explained below in more detail in descriptions related to FIG. 5.

The connector 130 may be coupled to the other, opposite end of the body 110. The connector 130 may be a connection device for electrically connecting an external cable or wire (see the reference numeral 310 in FIG. 8A) outside the microwave probe 100 to the body 110. The connector 130 may be an RF connector transferring an RF signal such as microwaves and the like. For example, the connector 130 may include SubMiniature A (SMA), SubMiniature B (SMB), N type, Bayonet Neil-Concelman (BNC), TNC, 7/16 DIN connectors, and the like. Of course, the connector 130 is not limited to the connectors set forth above. The external wire connected to the connector 130 may be an RF cable, for example, an RG 58, RG 316, RG 400, RG 402, RG 405, SF/SR 085, SF/SR 141, LMR 200 cable, or the like. Of course, the external wire is not limited to the RF cables set forth above.

The connector 130 may be omitted from the microwave probe 100 according to the present example embodiment. For example, the body 110 of the microwave probe 100 may be directly connected to a network analyzer (see the reference numeral 300 in FIG. 15). That is, the body 110 may be directly connected to a connector mounted on the network analyzer. Here, the body 110 may be formed, for example, in an RF cable structure. The network analyzer may generate a microwave to transfer the microwave to the outside thereof, and may receive a signal transferred from the outside thereof to detect a resonant frequency or the like.

The microwave probe 100 according to the present example embodiment may be non-invasively coupled to a viewport (see the reference numeral 220 in FIG. 15) of a chamber (see the reference numeral 200 in FIG. 15) in a plasma process. Here, the term "non-invasively" may mean that the microwave probe 100 is coupled to an outside of the chamber instead of invading or being inserted into the chamber. In addition, since the microwave probe 100 does not invade into the chamber and thus does not contact plasma, the non-invasive manner may also be referred to as a non-contact manner.

The microwave probe 100 may include a structure for coupling to the chamber. For example, the structure for coupling to the chamber may be formed on any one of the body 110, the head 120, and the connector 130. For example, a structure for various mechanical coupling, such as screw coupling, hook coupling, wedge coupling, snap coupling, and the like, may be mounted on the microwave probe 100, and a structure corresponding to the above structure may be mounted on a wall of the chamber, whereby the microwave probe 100 may be coupled to a viewport of the chamber using the coupling features or manners set forth above. A structure such as a vacuum sucker may be mounted on the microwave probe 100, whereby the microwave probe 100 may be coupled to the viewport of the chamber through a vacuum suction principle. In addition, the microwave probe 100 may also be coupled to the viewport of the chamber using an adhesive tape arranged on a surface of the head 120.

In some cases, the microwave probe 100 may be naturally coupled to the viewport of the chamber without a separate coupling means. For example, if the viewport is formed in a circular recessed structure, the head 120 may be formed to a similar size to or substantially the same size as the viewport and inserted into the viewport having the recessed structure, whereby the microwave probe 100 can be naturally coupled to the viewport of the chamber.

The microwave probe 100 according to the present example embodiment may be non-invasively coupled to the viewport of the chamber in a plasma process, and thus be used to monitor a plasma state inside the chamber. More specifically, the microwave probe 100 may be coupled to an outer surface of the viewport mounted on the chamber in such a manner that the microwave probe 100 contacts the outer surface of the viewport, whereby the microwave probe 100 can be easily coupled to the chamber without a change in shape of the viewport. In addition, the microwave probe 100 is non-invasively coupled to the outside of the chamber, whereby the microwave probe 100 itself does not affect the plasma state inside the chamber. Therefore, using the non-invasive microwave probe 100, a microwave is applied into the chamber, and signals generated inside the chamber are received, whereby the plasma state inside the chamber can be accurately detected and monitored. A principle of detecting and monitoring the plasma state inside the chamber using the microwave probe 100 will be described below in more detail with reference to FIG. 11.

Figure 2A:
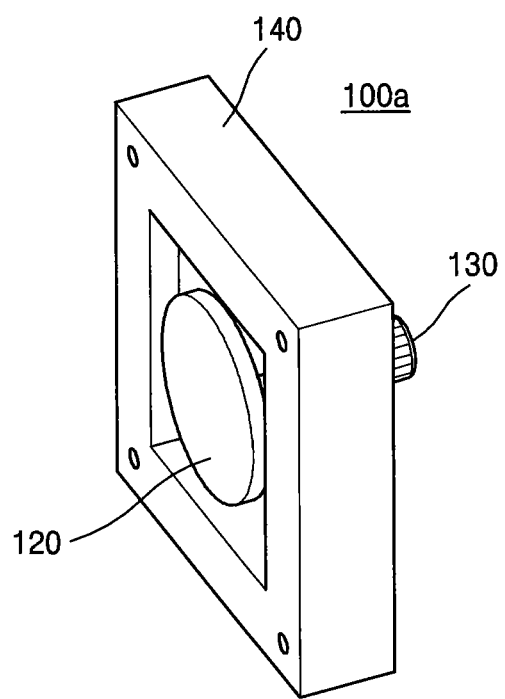
FIGS. 2A to 2D are a perspective view, plan views, and a sectional view of a microwave probe according to an example embodiment of the inventive concept.
Figure 2B:
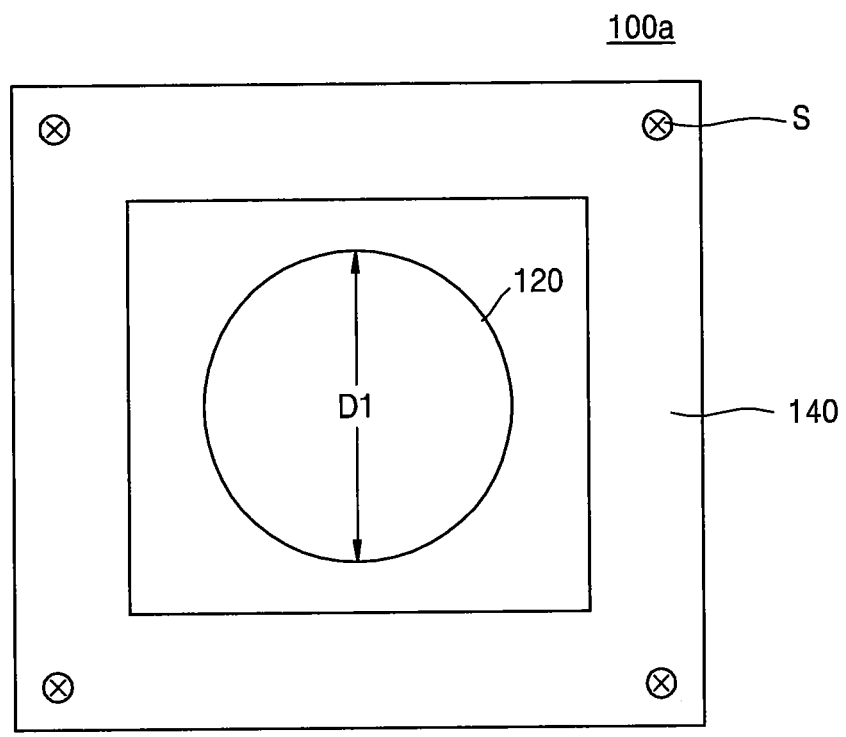
Figure 2C:
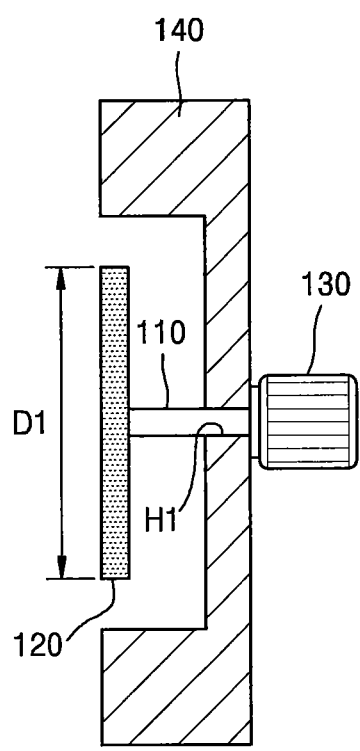
Figure 2D:
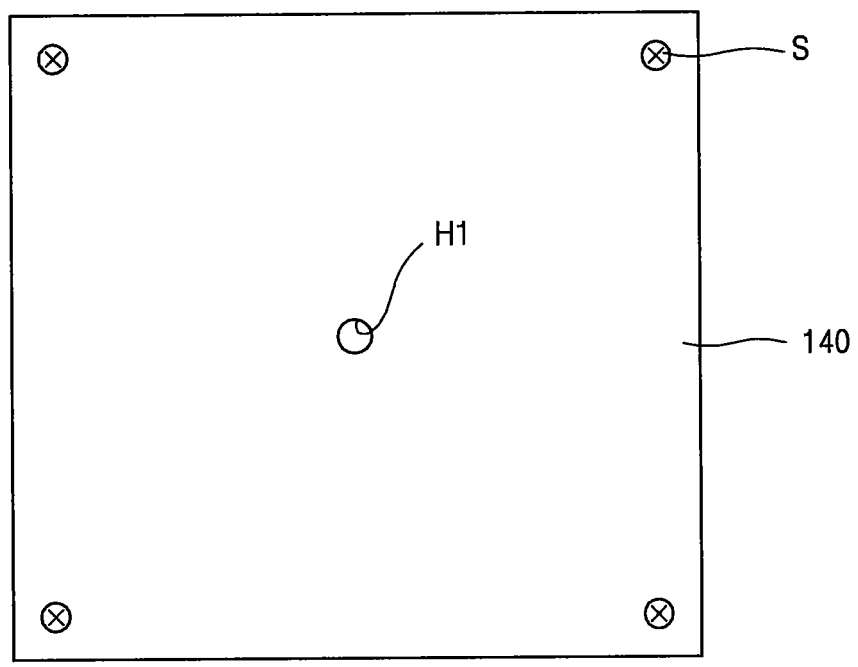

FIG. 2A is a perspective view of a microwave probe according to an example embodiment of the inventive concept, FIG. 2B is a plan view of the microwave probe when the microwave probe is viewed from a head side towards a connector, FIG. 2C is a sectional view of the microwave probe including the connector, and FIG. 2D is a plan view of the microwave probe when the microwave probe is viewed from a connector side towards the head after a body, the head, and the connector are removed from the microwave probe. In the interest of brevity, details which have been described above with reference to FIGS. 1A and 1B may be only briefly described or omitted.

Referring to FIGS. 2A to 2D, a microwave probe 100a according to the present example embodiment may differ from the microwave probe 100 of FIGS. 1A and 1B in that the microwave probe 100a further includes a ground cover 140. Specifically, the microwave probe 100a according to the present example embodiment may further include the ground cover 140 surrounding a body 110 and a head 120.

As shown in FIGS. 2A to 2D, the ground cover 140 may have a rectangular frame structure with one side closed such that a rim or outer sidewall of the ground cover 140 protrudes or extends from a base of the ground cover 140 to surround the body 110 and the head 120. A through-hole H1 may be formed in a central portion of the ground cover 140, and the body 110 may extend through the through-hole H1 to be connected to a connector 130 external to the ground cover 140. In some cases, the through-hole H1 is formed to have a larger size in the ground cover 140, and the connector 130 may be inserted into the through-hole H1.

Figure 8A:
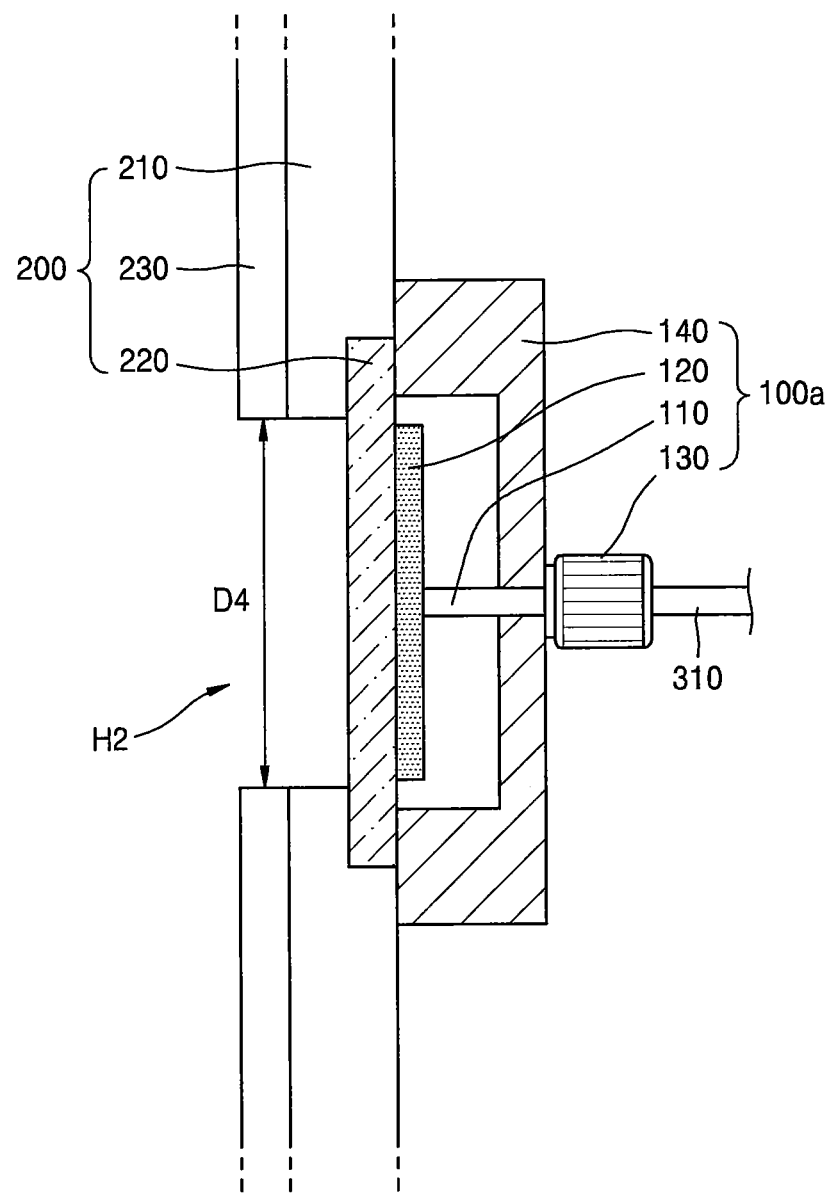
FIGS. 8A and 8B are a sectional view and a plan view of the microwave probe of FIG. 2A, which is coupled to a chamber.

The rim of the ground cover 140 may be brought into tight contact with a wall of a chamber (200 in FIG. 15) to be coupled (e.g., by a fastener such as a screw) to the chamber. Thus, a screw hole S may be formed in a portion of the ground cover 140. Of course, in the ground cover 140, a structure for hook coupling, wedge coupling, snap coupling, or the like may be formed instead of a structure for screw coupling. As shown in FIG. 8A, when the ground cover 140 is coupled to a wall 210 of the chamber 200, a surface of the head 120 may contact an outer surface of a viewport 220 of the chamber 200.

The ground cover 140 may include a conductive material, for example, a metal such as Cu, Al, and the like. The overall ground cover 140 may be a metal, or only a surface of the ground cover 140 may be a metal. The ground cover 140 may maintain a grounded state in a plasma process. The ground cover 140 alone may be grounded by directly connecting the ground cover 140 to a ground, and the ground cover 140 and the wall of the chamber may be grounded together by coupling the ground cover 140 to the wall of the chamber connected to a ground.

The ground cover 140 in a grounded state can block radiation of plasma light from the viewport of the chamber, and prevent a noise external to the microwave probe 100a from entering or flowing into the head 120. Due to the presence of the ground cover 140, a reception efficiency of the head 120 for signals generated inside the chamber can be improved. Thus, measurement sensitivity of a surface wave resonant frequency can be improved. In addition, as described above, the body 110 includes the insulation covering layer 114, whereby the external noise can be prevented from entering or flowing in the metal layer 112. Further, the head 120 may be formed in a thin film disk shape that contacts the viewport of the chamber, thereby further improving the reception efficiency of the head 120.

As a result, the microwave probe 100a according to the present example embodiment includes the body 110 including the insulation covering layer 114, the disk-shaped head 120, and the ground cover 140 which can maintain a grounded state while covering the body 110 and the head, thereby maximizing a reception efficiency for signals generated inside the chamber, for example, measurement sensitivity for a surface wave resonant frequency.

Figure 3A:
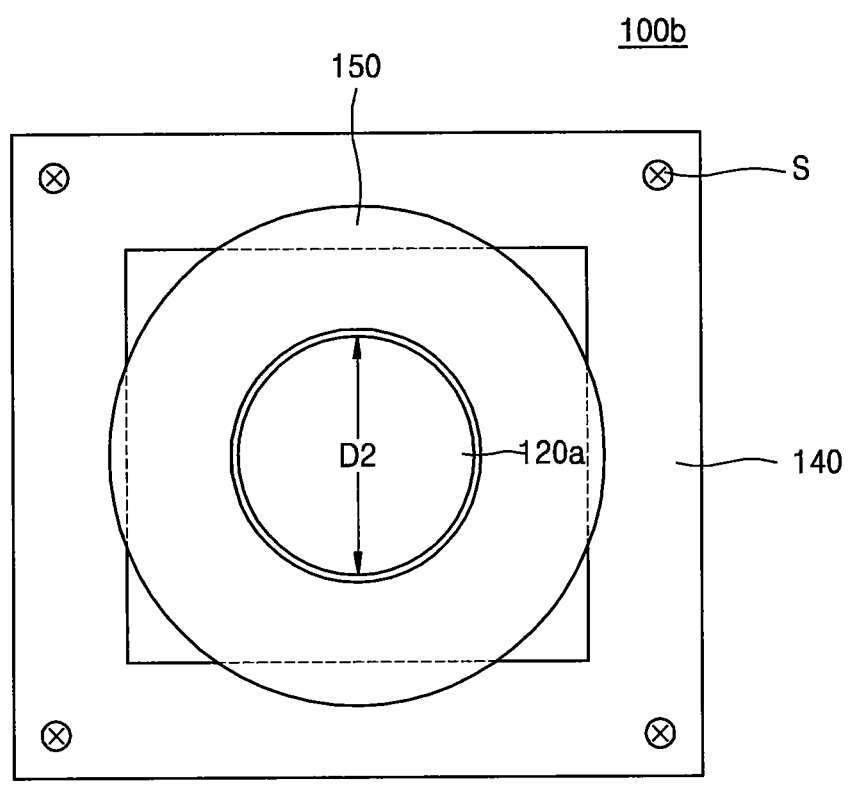
FIGS. 3A and 3B are a plan view and a sectional view of a microwave probe according to an example embodiment of the inventive concept.
Figure 3B:
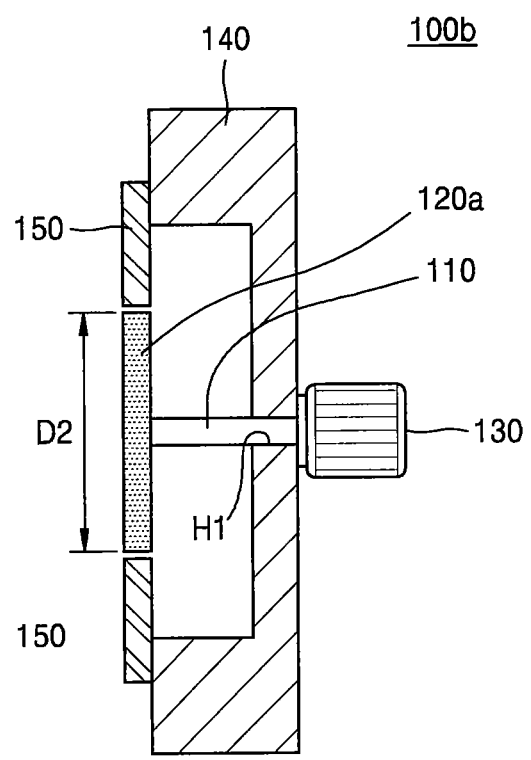

FIGS. 3A and 3B are a plan view and a sectional view of a microwave probe according to an example embodiment of the inventive concept. FIG. 3A is a plan view of the microwave probe when the microwave probe is viewed from a head side towards a connector. In the interest of brevity, details which have been described above with reference to FIGS. 1A to 2D may be only briefly described or omitted.

Referring to FIGS. 3A and 3B, a microwave probe 100b according to the present example embodiment may differ from the microwave probe 100a of FIG. 2A in that the microwave probe 100b further includes a filter 150. In addition, a head 120a of the microwave probe 100b may have an area that is different from the area of the head 120 of the microwave probe 100a of FIG. 2A.

In the microwave probe 100b, the head 120a may have a second diameter D2, and the second diameter D2 may be less than the first diameter D1 of the head 120 of the microwave probe 100 or 100a of FIG. 1A or 2A. For example, the second diameter D2 of the head 120a may range from about 2 cm to about 3 cm. If a viewport (see the reference numeral 220 in FIG. 15) of a chamber (see the reference numeral 200 in FIG. 15) has a diameter of about 5 cm, the head 120a may have a second diameter D2 that is 75% or less of the diameter of the viewport.

As such, if the head 120a has a relatively small area, when the microwave probe 100b is coupled to the chamber, an outer portion of the viewport may not contact the head 120a and may be exposed. In a plasma process, plasma light may be radiated through the exposed portion of the viewport.

In a plasma process, a plasma state inside the chamber may be directly confirmed by an eye in some cases. Here, the outer portion of the viewport, which does not contact the head 120a and is exposed, may be used to confirm the plasma state. Plasma light may include ultra-violet (UV) light which can damage eyesight or a skin. Therefore, a filter to block UV light may be desirable.

The microwave probe 100b according to the present example embodiment may include the filter 150, for example, a UV filter capable of blocking UV light. The filter 150 may have a shape surrounding an outer portion of the head 120a. Specifically, the filter 150 may have a circular disk shape in which a central portion is empty (e.g., a ring shape). The head 120a may be inserted into the central portion of the filter 150, and thus be surrounded by the filter 150. For example, the central portion of the filter 150 may have a circular shape like the head 120a, and the central open portion may have an area that is almost equal to or slightly greater than an area of the head 120a.

Figure 9A:
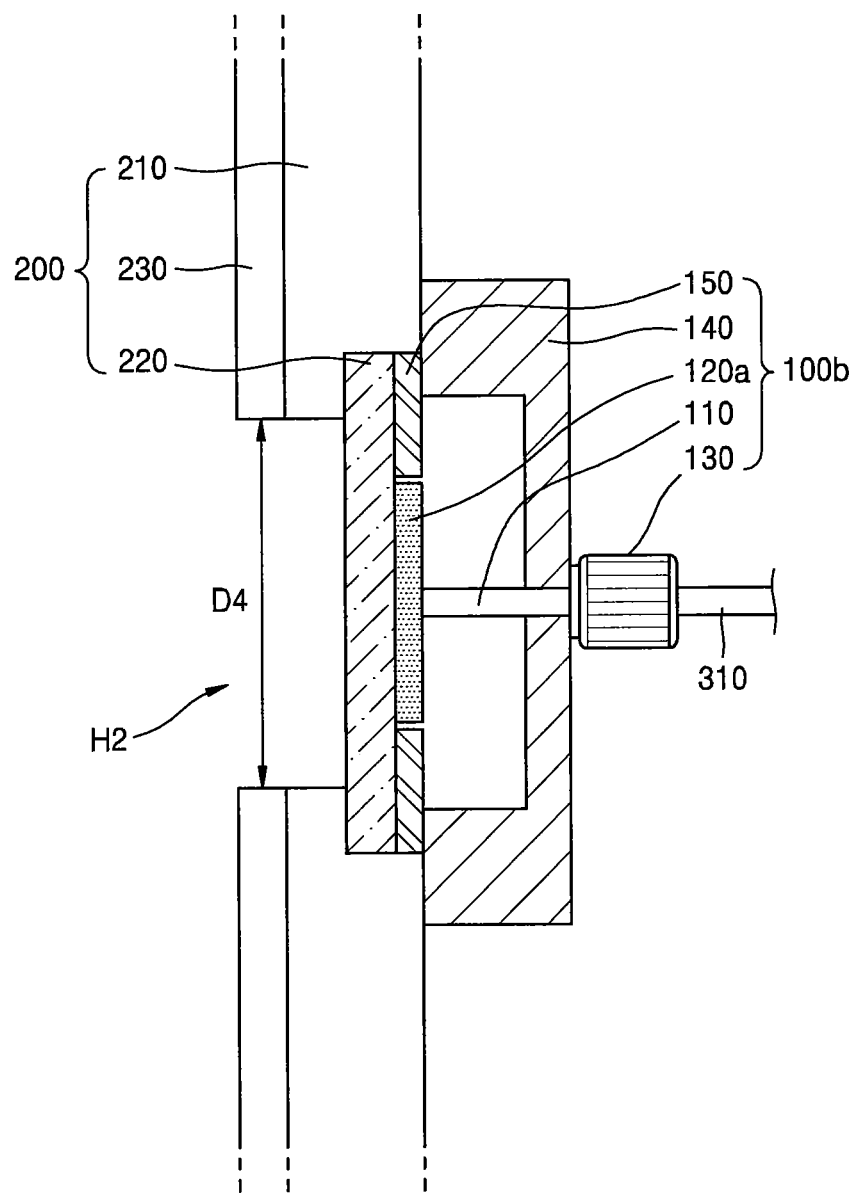
FIGS. 9A and 9B are a sectional view and a plan view of the microwave probe of FIG. 3A, which is coupled to a chamber.
Figure 9B:
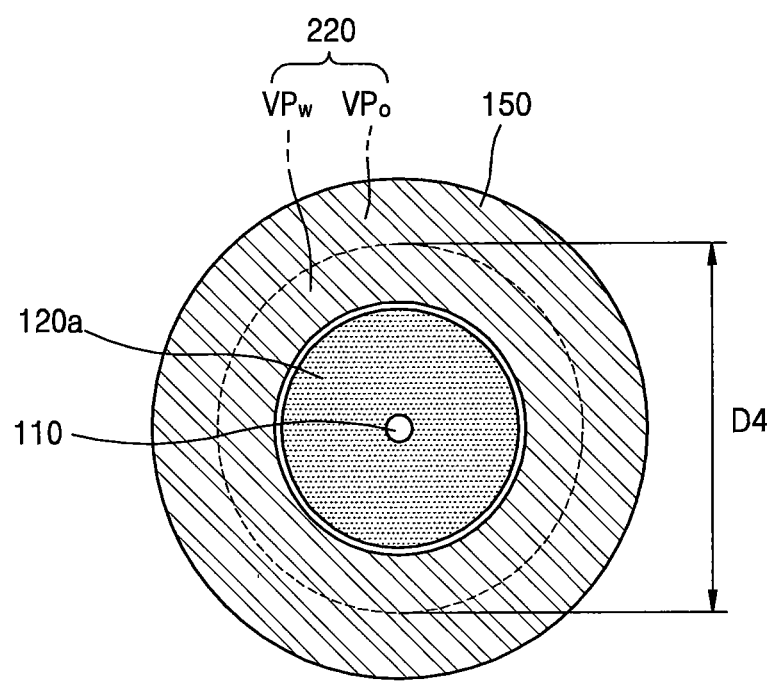

As shown in FIGS. 9A and 9B, the filter 150 may have a shape and a size that are similar to those of the viewport. Thus, the filter 150 can cover the outer portion of the viewport, which does not contact the head 120a. In some cases, although the filter 150 may have a smaller size than the viewport, the filter 150 may have a larger size than a window region (see the reference numeral VPw in FIG. 9B) of the viewport, through which light passes.

The filter 150 may be included in or on the microwave probe 100b in a state of being coupled to a ground cover 140 via an adhesive or the like. In addition, if the viewport is formed in a circular recessed structure on the chamber, the filter 150 may be inserted into the recess-structured viewport separately from the ground cover 140, and when the microwave probe 100b is coupled to the chamber, the filter 150 may contact the ground cover 140 to be included in or on the microwave probe 100b.

The microwave probe 100b according to the present example embodiment includes the relatively small head 120a and the filter 150 surrounding the head 120a, whereby a plasma state can be confirmed by an eye through the viewport at an outer side of the head 120a while signals can be received through the head 120a. In addition, a UV filter blocking UV light is used as the filter 150, thereby protecting an eye from UV light. For reference, a window portion, through which light can penetrate, may be formed in a portion of the ground cover 140, and a plasma state may be confirmed using the window portion. In addition, in some cases, a plasma state may be confirmed while the ground cover 140 is separated from the microwave probe 100b.

Figure 4A:
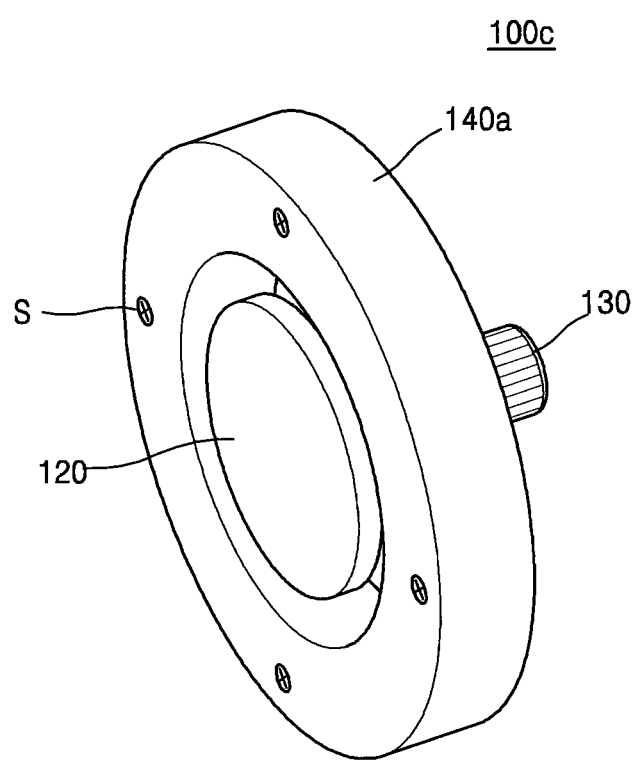
FIGS. 4A and 4B are a perspective view and a plan view of a microwave probe according to an example embodiment of the inventive concept.
Figure 4B:
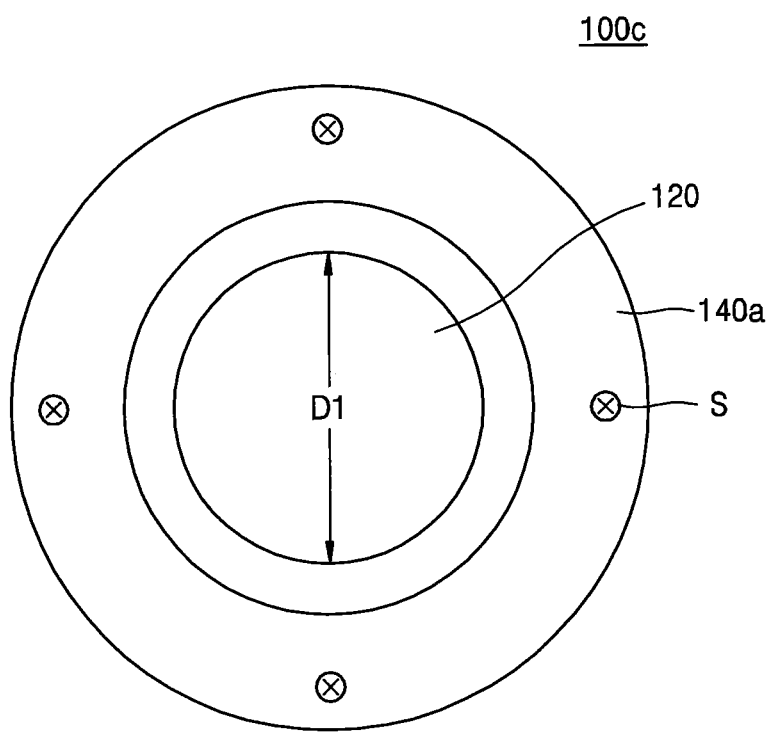

FIGS. 4A and 4B are a perspective view and a plan view of a microwave probe according to an example embodiment of the inventive concept, and FIG. 4B is a plan view of the microwave probe when the microwave probe is viewed from a head side towards a connector. In the interest of brevity, details which have been described above with reference to FIGS. 1A to 2D may be only briefly described or omitted.

Referring to FIGS. 4A and 4B, a microwave probe 100c according to the present example embodiment may differ from the microwave probe 100a of FIG. 2A in terms of a shape of a ground cover 140a. For example, in the microwave probe 100c, the ground cover 140a may have a circular frame structure with one side closed. In addition, a rim or sidewall of the ground cover 140a may protrude or extend from a base of the ground cover 140a to surround a body 110 and a head 120.

Fastener holes such as screw holes S for screw coupling may be formed in the rim of the ground cover 140a. Of course, a structure for hook coupling, wedge coupling, snap coupling, or the like may be formed in the ground cover 140a instead of a structure for screw coupling. Generally, since a viewport (220 in FIG. 15) of a chamber (200 in FIG. 15) has a circular shape in most cases, the ground cover 140a may be formed in a circular shape to symmetrically cover the viewport.

In the microwave probe 100c, the shape of the ground cover 140a is not limited to the circular shape. For example, the ground cover 140a may have various shapes, such as an ellipse, polygon, and the like, based on the shape of the viewport.

Figure 5:
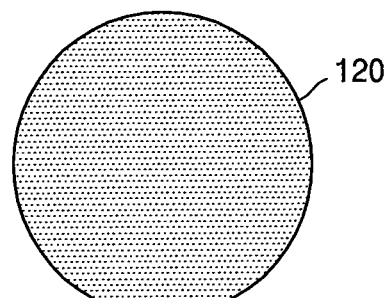
FIG. 5 illustrates plan views of various shapes of head surfaces of microwave probes according to example embodiments of the inventive concept.
Figure 5:
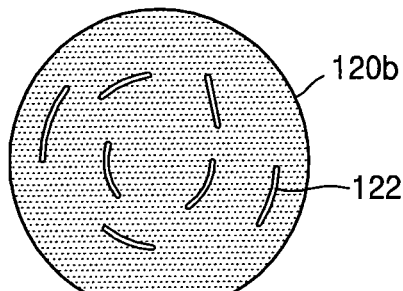
Figure 5:
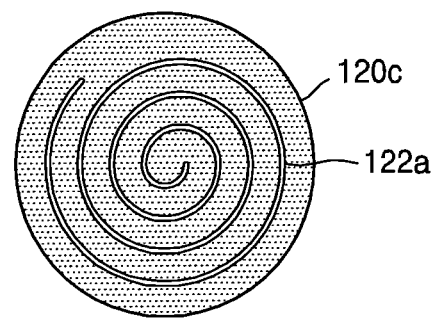
Figure 5:
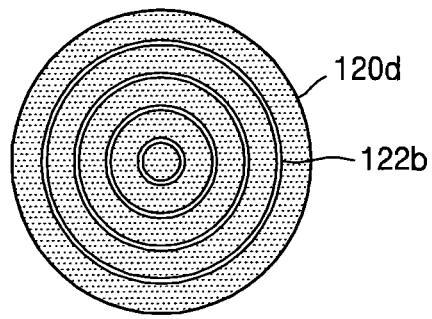
Figure 5:
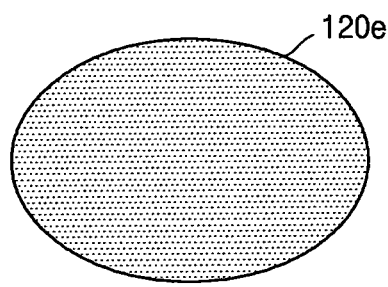
Figure 5:
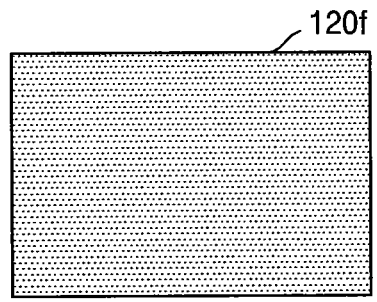

FIG. 5 shows plan views of various shapes of head surfaces of microwave probes according to example embodiments of the inventive concept. In the interest of brevity, details which have been described above with reference to FIGS. 1A and 1B may be only briefly described or omitted.

Referring to FIG. 5, a head 120 of FIG. 5(a) is a head having the most fundamental structure. The head 120 may be formed in a circular flat plate structure, and may not include any pattern on a surface thereof. For example, patterns such as grooves may not be formed on the surface of the head 120, which contacts a viewport (220 in FIG. 8A) of a chamber (200 in FIG. 8A), and the surface of the head 120 may be maintained in a smooth state.

A head 120b of FIG. 5(b) may include irregular patterns on a surface thereof. For example, a large number of grooves 122 having a straight line or curve shape may be formed on the surface of the head 120b. The grooves 122 are formed on the surface of the head 120b, such that an efficiency of microwave application and/or signal reception through the head 120b can be improved.

A head 120c of FIG. 5(c) may include a spiral pattern on a surface thereof. For example, a spiral groove 122a may be formed on the surface of the head 120c. The spiral groove 122a is formed on the surface of the head 120c, such that an efficiency of microwave application and/or signal reception through the head 120c can be improved.

A head 120d of FIG. 5(d) may include a large number of concentric circular patterns on a surface thereof. For example, a large number of concentric circular grooves 122b may be formed on the surface of the head 120d. The concentric circular grooves 122b are formed on the surface of the head 120d, such that an efficiency of microwave application and/or signal reception through the head 120d can be improved.

Although the straight line or curve-shaped grooves, the spiral groove, and the concentric circular grooves on the surface of the head have been described above as examples, shapes of patterns on the surface of the head are not limited thereto. For example, to improve microwave application and/or signal reception efficiencies of the head, patterns having a wide variety of shapes may be formed on the surface of the head.

A head 120e of FIG. 5(e) may have an elliptical flat plate structure, and a head 120f of FIG. 5(f) may have a rectangular flat plate structure. Of course, the shape or structure of the head is not limited to the flat plate structures set forth above. For example, the head may have various shapes such as triangular flat plates, pentagonal flat plates, and the like.

In the microwave probe according to the present example embodiment, the shape of the head may be variously changed in consideration of a shape of the viewport with which the head is brought into contact, or improvement in efficiencies of microwave application and/or signal reception. In addition, in the microwave probe according to the present example embodiment, the structure of the head is not limited to flat plates. For example, in some cases, the head may have a probe shape instead of a flat plate shape. In the head having a probe shape, instead of separately forming the head, a portion of an end of the metal layer 112 of the body 110 may act as the head.

Figure 6:
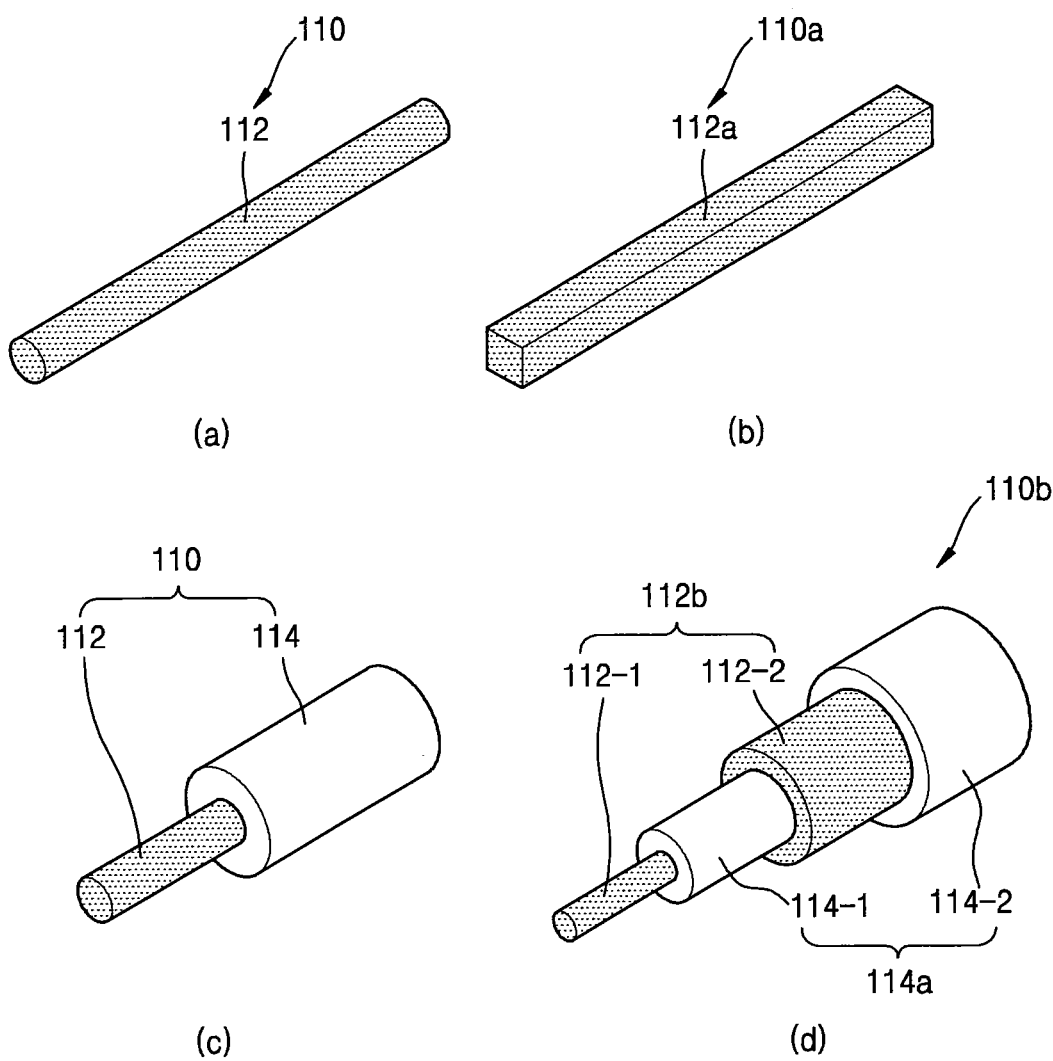
FIG. 6 illustrates perspective views of various shapes of bodies of microwave probes according to example embodiments of the inventive concept.

FIG. 6 shows perspective views of various shapes of bodies of microwave probes according to example embodiments of the inventive concept. In the interest of brevity, details which have been described above with reference to FIGS. 1A and 1B may be only briefly described or omitted.

Referring to FIG. 6, FIG. 6(a) shows a metal layer 112 of a body 110, and the metal layer 112 may have a circular pillar or cylindrical shape extending in one direction. As described above, the metal layer 112 may include a metal having good conductivity, for example, Cu, Al, or the like. The metal layer 112 may have a thickness of about 1 mm and a length of a few centimeters. Of course, the thickness and the length of the metal layer 112 are not limited to the numerical values set forth above.

FIG. 6(b) shows a metal layer 112a having a rectangular or quadrangular pillar shape, and the metal layer 112a may have a thickness and a length, which are similar to those of the metal layer 112 of FIG. 6(a). For reference, the thickness may refer to a diameter when the metal layer is a circular pillar, and the thickness may refer to a length of a shorter side when the metal layer is a rectangular pillar. Although the circular pillar and quadrangular pillar shapes are illustrated as examples of structures of the metal layers 112, 112a in FIGS. 6(a) and 6(b), the structure of the metal layer is not limited thereto. For example, the metal layer may also be formed in an elliptical pillar shape or a polygonal pillar shape other than a quadrangular pillar shape. The metal layer 112 of FIG. 6(a) itself and the metal layer 112a of FIG. 6(b) itself may respectively constitute bodies 110, 110a without insulation covering layers on outer sides thereof.

FIG. 6(c) shows a structure of a fundamental body 110, and the body 110 may include an inner metal layer 112 and an outer insulation covering layer 114. The metal layer 112 may have a circular pillar shape like the metal layer 112 of FIG. 6(a). Of course, the metal layer 112 may have a quadrangular pillar shape like the metal layer 112a of FIG. 6(b), or may have other polygonal pillar shapes. The insulation covering layer 114 surrounds the metal layer 112, and includes an insulating material for insulating the metal layer 112, as described above.

FIG. 6(d) shows a body 110b having a coaxial cable structure. The body 110b may include an inner metal layer 112-1, an inner insulating layer 114-1, an outer metal layer 112-2, and an outer insulating layer 114-2. The inner metal layer 112-1 and the outer metal layer 112-2 may constitute a metal layer 112b, and the inner insulating layer 114-1 and the outer insulating layer 114-2 may constitute an insulation covering layer 114a.

The coaxial cable structure may be used when a frequency of a transferred signal is high. More specifically, since the coaxial cable exhibits low attenuation of a signal at up to a high frequency, the coaxial cable is suitable for broadband transmission. In addition, the coaxial cable can exhibit low leakage or loss of a signal due to the presence of the outer metal layer 112-2. The inner insulating layer 114-1 may generally include polyethylene, and may include a circular plate-shaped spacer when the cable is thick. In addition, when used in the cable for the purpose of a high temperature, the inner insulating layer 114-1 may include teflon. Since materials, signal transfer properties, and the like of the coaxial cable are known in the art, further details thereof will be omitted herein.

The bodies of the microwave probes 100, 100a, 100b, 100c according to the present embodiment may have a coaxial cable structure like the body 110b of FIG. 6(d). Thus, the bodies of the microwave probes 100, 100a, 100b, 100c can stably transfer signals of relatively high frequencies. In addition, an external cable or wire (see the reference numeral 310 in FIG. 8A) connected to the connectors (130 in FIG. 1A, and the like) may also be formed in a coaxial cable structure. Such a coaxial cable structure is mainly used for an RF cable which transfers RF signals.

Figure 7A:
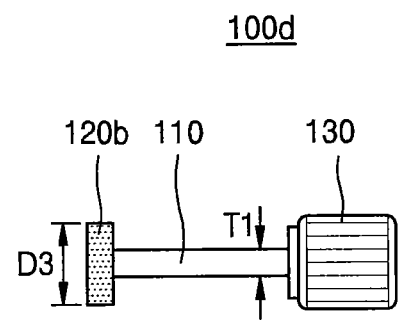
FIGS. 7A and 7B are sectional views of microwave probes according to example embodiments of the inventive concept.
Figure 7B:
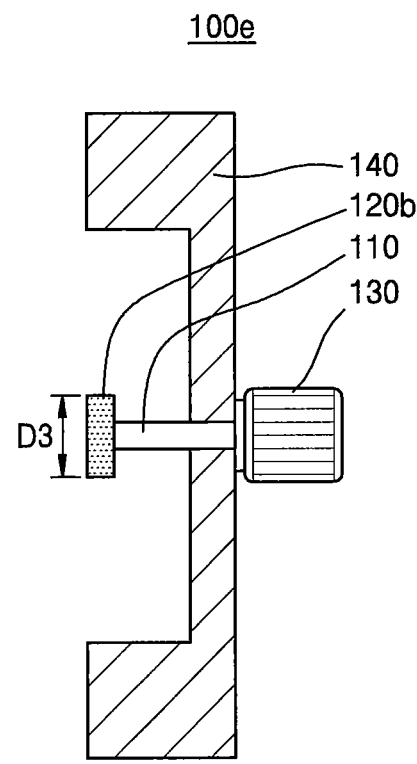

FIGS. 7A and 7B are sectional views of microwave probes according to example embodiments of the inventive concept. In the interest of brevity, details which have been described above with reference to FIGS. 1A to 6 may be only briefly described or omitted.

Referring to FIG. 7A, a microwave probe 100d according to the present example embodiment may differ from the microwave probe 100 of FIG. 1A in terms of a structure of a head 120b. In the microwave probe 100d, the head 120b may have a considerably smaller area. For example, a third diameter D3 of the head 120b may be not more than three times a first thickness T1 of a body 110. In some cases, the third diameter D3 of the head 120b may be almost or substantially the same as the first thickness T1 of the body 110. Furthermore, the third diameter D3 of the head 120b may be almost or substantially the same as a thickness of a metal layer 112 of the body 110. When the third diameter D3 of the head 120b is substantially the same as the thickness of the metal layer 112 of the body 110, a portion of the metal layer 112 may be used as the head without separately forming the head, and the head 120b may have a probe shape.

Figure 12A:
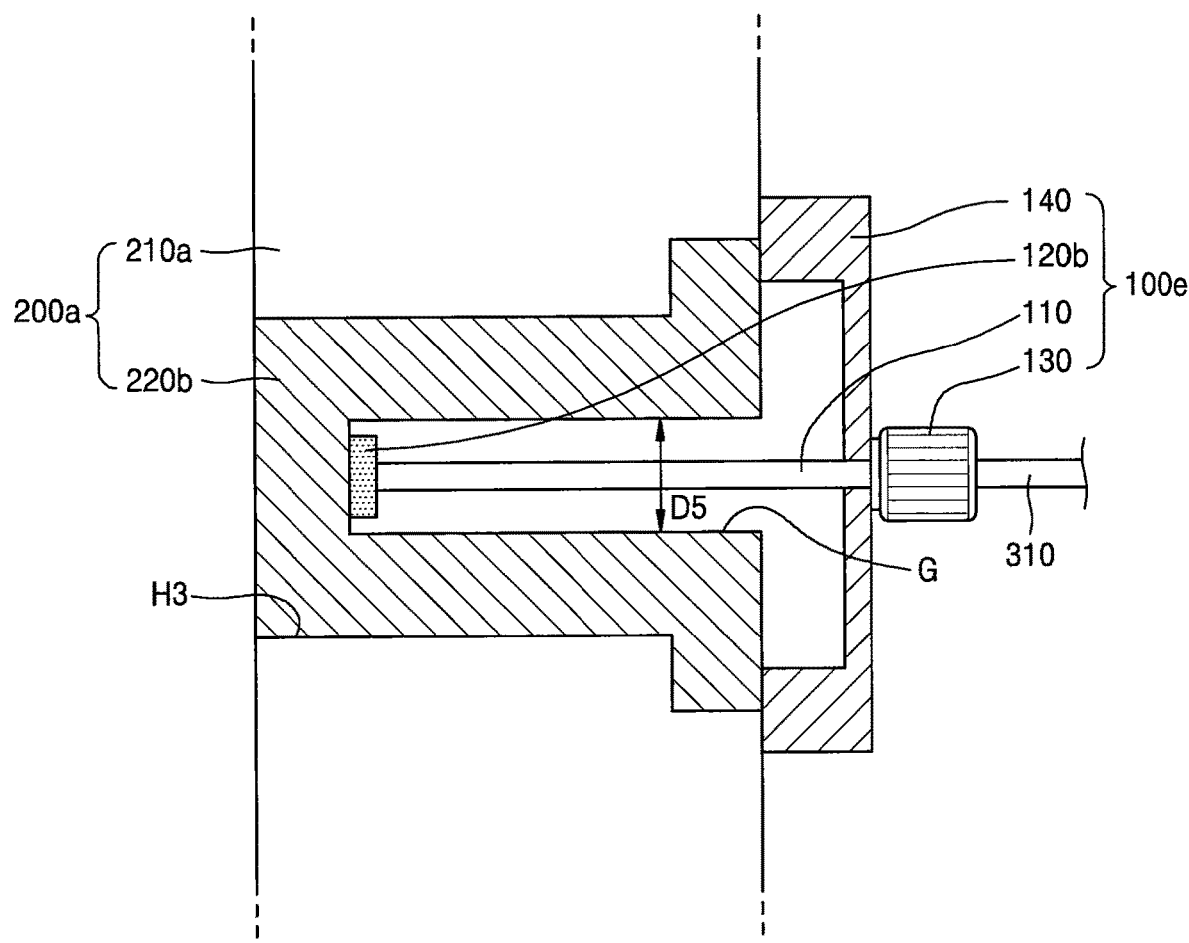
FIGS. 12A and 12B are sectional views of microwave probes according to example embodiments of the inventive concept, which are coupled to differently-shaped viewports included in chambers.
Figure 12B:
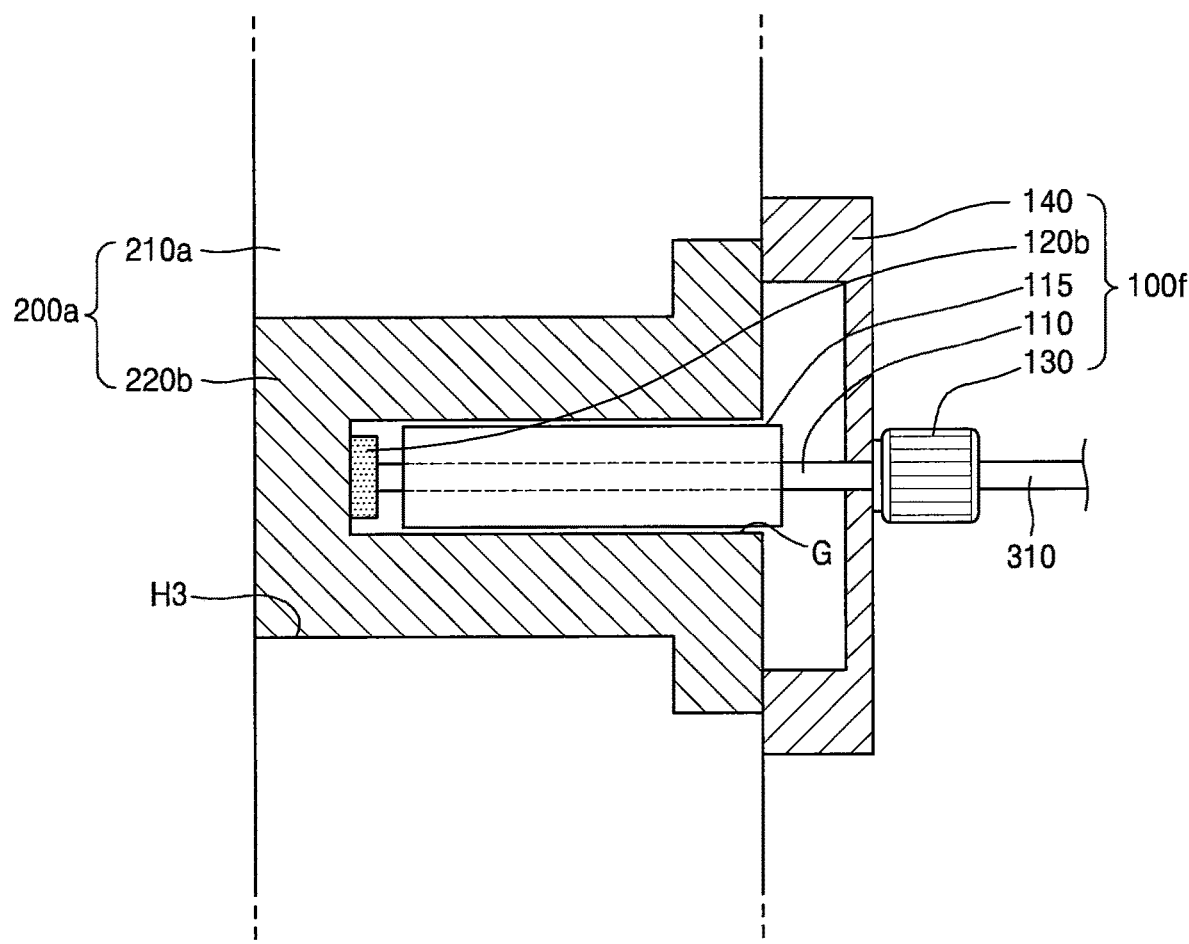

When a viewport 220b has a groove or channel in a central portion thereof, the head 120b of the microwave probe 100d may be sized to be inserted into and coupled to the groove of the viewport 220b, as shown in FIG. 12A or 12B. In addition, an area of the head 120b may vary with an area of a bottom or end surface of the groove of the viewport 220b. For example, the area of the head 120b may be substantially the same as the area of the bottom surface of the groove of the viewport 220b. Thus, if an area of the groove of the viewport 220b is similar to an area of the body 110 of the microwave probe 100d, the head 120b may have almost or substantially the same diameter as a cross section of the body 110.

Referring to FIG. 7B, a microwave probe 100e according to the present example embodiment may differ from the microwave probe 100a of FIG. 2A in terms of a structure of a head 120b. In the microwave probe 100e, the head 120b may have a considerably smaller area like the microwave probe 100d of FIG. 7A. When a viewport 220b has a groove in the central portion thereof, the microwave probe 100e may also provide a structure which can be easily coupled to the viewport 220b. Specifically, the head 120b may be inserted into the groove of the viewport 220b, and a ground cover 140 may be coupled to an outer wall of a chamber through fastener (e.g., screw) coupling or the like, such that the microwave probe 100e may be coupled to the viewport 220b of the chamber.

Figure 8B:
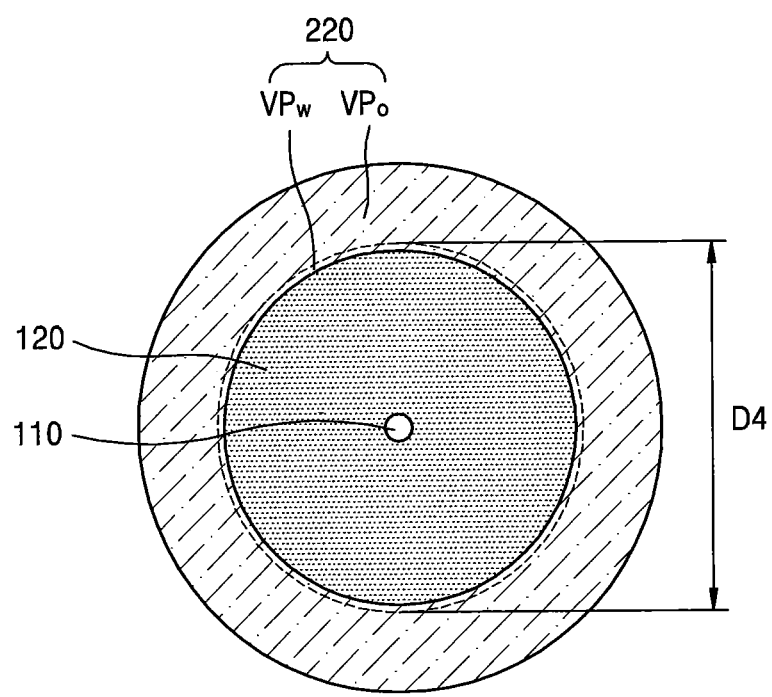

FIGS. 8A and 8B are a sectional view and a plan view of the microwave probe of FIG. 2A, which is coupled to a chamber. FIG. 8B is the plan view of the microwave probe of FIG. 2A when the microwave probe of FIG. 2A is viewed from a connector side towards the head, and the connector, the ground cover, the chamber wall, and the like are omitted in FIG. 8B for clarity. In the interest of brevity, details which have been described above with reference to FIGS. 1A to 7B may be only briefly described or omitted.

Referring to FIGS. 8A and 8B, the microwave probe 100*a* according to the present example embodiment may be coupled to a viewport 220 of a chamber 200. The chamber 200 may include a wall 210 such as an outer wall for isolating an inside of the chamber from an outside of the chamber, and may include a through-hole H2 penetrating through the wall 210 in a portion to which the viewport 220 is mounted. The viewport 220 may be coupled to the wall 210 to cover or fill the through-hole H2. Since the viewport 220 also serves to isolate the inside of the chamber from the outside of the chamber, the viewport 220 may be included in the wall of the chamber.

Since the viewport 220 includes a material such as quartz ($SiO_2$), sapphire ($Al_2O_3$), or the like, plasma light inside the chamber may be radiated to the outside of the chamber through the viewport 220. Thus, the inside of the chamber or plasma light may be visually observed through the viewport 220, or an optical apparatus capable of detecting plasma light may be mounted on the viewport 220, thereby detecting plasma light through the optical apparatus.

As shown in FIG. 8B, the viewport 220 may include a window region VPw corresponding to the through-hole H2 and an outer region VPo. The window region VPw may be a region through which plasma light radiated through the through-hole H2 is transmitted, and the outer region VPo may be a region which is brought into contact with and coupled to the wall 210 of the chamber 200. In other words, the first diameter (D1 in FIG. 2C) of the head 120 may be almost the same as or slightly less than a fourth diameter D4 of the window region VPw. In some cases, the first diameter D1 of the head 120 may be greater than the fourth diameter D4 of the window region VPw. As such, the head 120 may be coupled to the viewport 220 to cover the overall window region VPw, thereby improving signal transfer properties of the microwave probe 100*a*. In particular, since plasma generated inside the chamber 200 is directly transferred to the window region VPw of the viewport 220 through the through-hole H2, the head 120 can more accurately detect a plasma state.

The ground cover 140 may be coupled to the wall 210 of the chamber 200 through fastener (e.g., screw) coupling or the like. As shown in FIG. 8A, an outer surface of the wall 210 of the chamber 200 may be in the same plane as an outer surface of the viewport 220. Thus, the ground cover 140 may be coupled to the chamber 200 to contact both the outer surface of the viewport 220 and the outer surface of the wall 210 of the chamber 200. In some cases, the outer surface of the viewport 220 may be closer to the inside of the chamber 200 than the outer surface of the wall 210 of the chamber 200. With this structure, the ground cover 140 may be coupled to the chamber 200 to contact only the wall 210 of the chamber 200.

For reference, the wall 210 of the chamber 200 may generally include a metal material, and may be maintained in a grounded state to block noises from the outside of the chamber 200 in a plasma process. An insulating liner 230 may be arranged on an inner side or surface of the wall 210 of the chamber 200. The insulating liner 230 may protect the wall 210 of the chamber 200 and cover metal structures protruding from the wall 210, thereby preventing arcing inside the chamber. The insulating liner 230 may include ceramic, quartz, or the like. For example, the insulating liner 230 may have a structure in which yttrium oxide ($Y_2O_3$) is coated onto sapphire ($Al_2O_3$).

FIGS. 9A and 9B are a sectional view and a plan view of the microwave probe of FIG. 3A, which is coupled to a chamber. FIG. 9B is the plan view of the microwave probe of FIG. 3A when the microwave probe of FIG. 3A is viewed from a connector side towards the head, and the connector, the ground cover, the chamber wall, and the like are omitted in FIG. 9B for clarity. In the interest of brevity, details which have been described above with reference to FIGS. 1A to 8B may be only briefly described or omitted.

Referring to FIGS. 9A and 9B, the microwave probe 100*b* according to the present example embodiment may also be coupled to the viewport 220 of the chamber 200. As described above, the head 120*a* of the microwave probe 100*b* may be smaller than the head 120 of the microwave probe 100*a* of FIG. 2A, and the microwave probe 100*b* may further include the filter 150 outside or around the head 120*a*. Thus, the microwave probe 100*b* may be coupled to the viewport 220 of the chamber 200 such that the outer surface of the viewport 220 is covered with the head 120*a* and the filter 150.

More specifically, the head 120*a* may cover a portion of the window region VPw of the viewport 220, and the filter 150 may cover another portion of the window region VPw, which is not covered with the head 120*a*, and the outer region VPo. In some cases, the filter 150 may have a smaller size in shape than the viewport 220, and thus may cover only a portion of the outer region VPo or may not cover the outer region VPo. The filter 150 covers the exposed window region VPw, which is not covered with the head 120*a*, and thus may block UV light and the like among plasma light. Thus, the outer region VPo, through which plasma light is not transmitted, may not be covered or entirely covered.

In the microwave probe 100*b*, the ground cover 140 may also be coupled to the wall 210 of the chamber 200 through fastener (e.g., screw) coupling or the like. As shown in FIG. 9A, the outer surface of the wall 210 of the chamber 200 may be in the same plane as an inner surface of the filter 150. Thus, the ground cover 140 may be coupled to the chamber 200 to contact both the inner surface of the filter 150 and the outer surface of the wall 210 of the chamber 200. As shown in FIG. 8A, the outer surface of the wall 210 of the chamber 200 may be in the same plane as the outer surface of the viewport 220. In this structure, the filter 150 may have a smaller size in external shape (e.g., smaller diameter) than the viewport 220, and the ground cover 140 may contact both the outer surface of the viewport 220 and the outer surface of the wall 210 of the chamber 200. In this case, the ground cover 140 may surround the head 120*a* and the filter 150.

Figure 10:
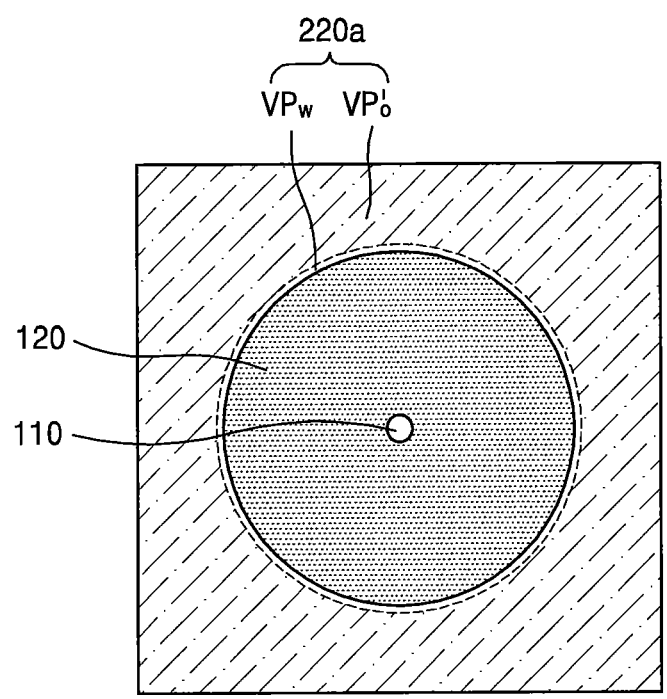
FIG. 10 is a plan view of the microwave probe of FIG. 2A, which is coupled to a chamber.

FIG. 10 is a plan view of the microwave probe of FIG. 2A, which is coupled to a chamber, when the microwave probe of FIG. 2A is viewed from a connector side towards the head, and the connector, the ground cover, the chamber wall, and the like are omitted in FIG. 10 for clarity. In the interest of brevity, details which have been described above with reference to FIGS. 1A to 9B may be only briefly described or omitted.

Referring to FIG. 10, the microwave probe 100*a* according to the present example embodiment may have the same structure as the microwave probe 100*a* of FIG. 8A. However, a viewport 220*a* to which the microwave probe 100*a* is coupled may differ in shape from the viewport 220 of FIG. 8B. For example, the viewport 220*a* may have a rectangular or square structure as shown in FIG. 10. The viewport 220*a* may include a window region VPw and an outer region VP'o. Since a shape of the window region VPw corresponds to the shape of the through-hole (H2 in FIG. 8A), the window region VPw may be substantially the same as the window region VPw of the viewport 220 of FIG. 8B. However, due to a difference in the shape of the viewport 220a, the outer region VP'o may differ in shape from the outer region VPo of the viewport 220 of FIG. 8B.

As described above, since the outer region VP'o is a region to which the wall 210 of the chamber 200 is coupled, the selection of the shape of the outer region VP'o may not have much consequence. Thus, the viewport 220a is not limited to circular or rectangular shapes, and may have a polygonal shape other than elliptical or rectangular shapes, for example.

Figure 11:
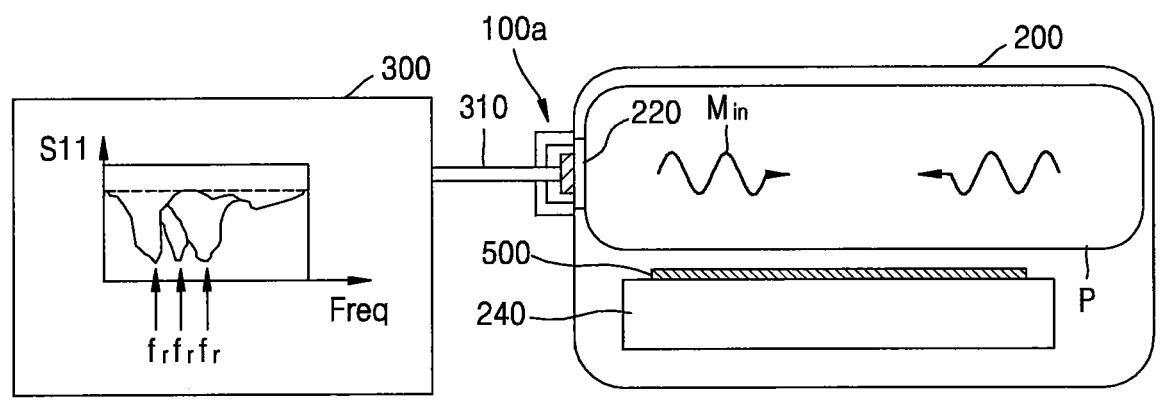
FIG. 11 is a conceptual diagram for explaining a method of detecting a plasma state inside a chamber using a microwave probe according to an example embodiment of the inventive concept.

FIG. 11 is a conceptual diagram for explaining a method of detecting a plasma state inside a chamber using a microwave probe according to an example embodiment of the inventive concept.

Referring to FIG. 11, a wafer 500 is disposed on an electrostactic chuck 240 inside the chamber 200, and plasma P is generated by injecting a process gas and applying RF power into the chamber, thereby performing a plasma process using the plasma P. For example, the plasma process may include etching, deposition, diffusion, surface treatment, novel material synthesis processes, and the like. The plasma process, particularly a semiconductor plasma process will be described in more detail in descriptions related to FIG. 15. The microwave probes according to the example embodiments of the inventive concept, for example, the microwave probe 100a of FIG. 2A may be coupled to the viewport 220 of the chamber 200. In addition, the microwave probe 100a may be connected to the network analyzer 300 through the external cable or wire 310 connected to the connector (see the reference numeral 130 in FIG. 2A).

The network analyzer 300 generates a microwave, and transfers the microwave to the microwave probe 100a through the external wire 310, thereby applying the microwave into the chamber 200 through the head (120 in FIG. 2A). The network analyzer 300 may be a commercial network analyzer. Since a resonant frequency of several hundred mega hertz (MHz) to a few giga hertz (GHz) is generally observed in a semiconductor plasma process, the network analyzer 300 can be used for the semiconductor plasma process as long as the network analyzer 300 can generate a microwave suitable for those conditions. The microwave may be transferred from a signal transmission port of the network analyzer 300 to the microwave probe 100a through the external wire 310.

The microwave $M_{in}$ that is input into the chamber 200 resonates at a specific frequency. Resonance may be sensed through a change in a measured value of a reflection coefficient S11. That is, as shown in a graph inside the network analyzer 300 at the left side in FIG. 11, specific peak values of a reflection coefficient S11 of an applied signal are observed, and frequencies corresponding to those peak values may be resonant frequencies $f_r$. Since frequencies other than a specific resonant frequency are fully reflected, the reflection coefficient S11 is almost 1.

Such a resonant frequency may be explained by resonance of a surface wave, and a resonant frequency of the surface wave is physically associated with a density of electrons generated in plasma. Thus, if the resonant frequency is known, the density of the electron generated in the plasma can be confirmed. A correlation between the resonant frequency of the surface wave and the electron density in the plasma can be described as follows.

First, an oscillation frequency ($f_{pe}$) of the plasma can be represented by Equation (1).

$$f_{pe} = 1/2\pi \cdot (e^2 N_e / \varepsilon_0 m_e)^{1/2} \quad \text{Equation (1)}$$

Here, e is a quantity of electric charge of an electron, $N_e$ is the number of electrons per unit volume (cm$^3$), that is, an electron density, $\varepsilon_0$ is a dielectric constant in vacuum, and $m_e$ is mass of an electron. e, $\varepsilon_0$, and $m_e$ are constants, and if values thereof are substituted, Equation (1) can be rearranged as Equation (2).

$$f_{pe}(\text{Hz}) \approx 8980 \cdot (N_e(\text{cm}^{-3}))^{1/2} \quad \text{Equation (2)}$$

The oscillation frequency ($f_{pe}$) of the plasma is proportional to an absorption frequency ($f_{abs}$) of the surface wave, that is, the resonant frequency of the surface wave. In other words, the oscillation frequency ($f_{pe}$) of the plasma and the absorption frequency ($f_{abs}$) of the surface wave may have a relation of Equation (3).

$$f_{pe} \propto f_{abs} \rightarrow f_{pe} = k f_{abs} \quad \text{Equation (3)}$$

Here, a proportional factor k is not a fixed value, but a value that varies with the viewport, the probe structure, measurement conditions, and the like. In other words, it is actually complicated to quantitatively determine the relation between the oscillation frequency ($f_{pe}$) of the plasma and the resonant frequency of the surface wave. However, the k value is experimentally and/or statistically determined, and the k value can then be utilized for the purpose of sensing a qualitative state change in monitoring for a plasma process.

Finally, if the resonant frequency of the surface wave, that is, the absorption frequency ($f_{abs}$) of the surface wave is detected, and the k value is experimentally and/or statistically determined, the electron density ($N_e$) of the plasma can be found by substituting Equation (2), which is an equation relating to the oscillation frequency ($f_{pe}$) of the plasma, into Equation (3). If a signal of the resonant frequency is actually measured by the network analyzer 300, the measured resonant frequency signal is transferred to a computer for analysis, and the computer finally calculates the electron density of the plasma using a analysis program. For example, the analysis program may be a program for calculating the electron density of the plasma using Equations (1) to (3), the value of the proportional factor k, and the like. In addition, the value of the proportional factor k may be experimentally and/or statistically determined based on the viewport, the probe structure, measurement conditions, and the like according to a corresponding plasma process. If the electron density of the plasma is calculated, a density, a state, and the like of the plasma in the plasma process can be accurately diagnosed.

The calculated electron density of the plasma may indicate a plasma state in the vicinity of the viewport 220 inside the chamber 200. In other words, the resonant frequency may be detected during the plasma process using the microwave probe 100a and the network analyzer 300, thereby sensing a plasma state in the vicinity of the wall (see reference numeral 210 in FIG. 8A) of the chamber 200, on which the viewport 220 is mounted, in real time. Finally, in the plasma process, the microwave probe 100a according to the present example embodiment can contribute to optimizing the plasma process by monitoring whether there is a problem in the plasma state in real time.

For reference, in an existing method of monitoring a plasma process, a probe is directly inserted into a chamber in an invasive manner. Such direct insertion of the probe cause process gases in use and generated reaction species to directly contact a surface of the probe during the plasma process, and thus has an influence on a situation of the plasma process. Thus, a distorted situation of the plasma process is monitored instead of an ideal situation thereof due to the invasive probe. In conclusion, the method of monitoring the plasma process by directly inserting the probe into the chamber is not suitable for industrial enterprises, and is limited to use for advanced research and development in university institutes, and the like.

On the other hand, each of the microwave probes 100, 100a to 100e according to the example embodiments of the inventive concept is non-invasively coupled to the viewport 220 of the chamber 200, thereby not affecting the plasma state inside the chamber 200. In addition, each of the microwave probes 100, 100a to 100e may include the body 110 including the insulation covering layer 114, and the disk-shaped head 120, thereby optimizing microwave application and/or a measurement sensitivity to signals generated inside the chamber. Further, each of the microwave probes 100, 100a to 100e may include the ground cover 140 which can maintain a grounded state while covering the body 110 and the head 120, thereby maximizing the measurement sensitivity to the signals by maximizing a signal-to-noise ratio (SNR).

FIGS. 12A and 12B are sectional views of microwave probes according to example embodiments of the inventive concept, which are coupled to differently-shaped viewports included in chambers. In the interest of brevity, details which have been described above with reference to FIGS. 1A to 10 may be only briefly described or omitted.

Referring to FIG. 12A, a microwave probe 100e according to the present example embodiment may be substantially the same as the microwave probe 100e of FIG. 7B. Thus, the microwave probe 100e may include the body 110, the head 120b, the connector 130, and the ground cover 140, and the head 120 may have a relatively small area. For example, the third diameter (D3 in FIG. 7A) of the head 120b may be not more than three times the first thickness (T1 in FIG. 7A) of the body 110. Of course, the diameter of the head 120b is not limited thereto.

The viewport 220b of the chamber 200a may have a structure in which the viewport 220b is inserted into a through-hole H3 in the wall 210a of the chamber 200a, and may include a groove or channel G in the central portion thereof. The groove G of the viewport 220b may have a cylindrical shape. Of course, the groove G of the viewport 220b is not limited to the cylindrical shape. A fifth diameter D5 of the groove G of the viewport 220b may be similar to or slightly greater than the third diameter D3 of the head 120b. The microwave probe 100e may be coupled to the chamber 200a such that the body 110 and the head 120b are inserted into the groove G of the viewport 220b.

As shown in FIG. 12A, the outer surface of the viewport 220b and the outer surface of the wall 210a of the chamber 200a may be in the same plane, and the ground cover 140 may be coupled to the chamber 200a to contact both the outer surface of the viewport 220b and the outer surface of the wall 210a of the chamber 200a. Of course, the outer surface of the viewport 220b may be closer to the inside of the chamber 200a than the outer surface of the wall 210a of the chamber 200a. In this case, the ground cover 140 may contact only the outer surface of the wall 210a of the chamber 200a. Of course, although not shown in FIG. 12A, the insulating liner 230 may be arranged on the inner side or surface of the wall 210a of the chamber 200a as in FIG. 8A or 9A.

Referring to FIG. 12B, a microwave probe 100f according to the present example embodiment may differ from the microwave probe 100e of FIG. 12A in that the microwave probe 100f further includes an outer cover layer 115. For example, the microwave probe 100f may further include the outer cover layer 115 surrounding the body 110. The outer cover layer 115 may have a cylindrical tube shape, and have a diameter that is about or almost the same as the fifth diameter D5 of the groove G of the viewport 220b. The outer cover layer 115 may include a metal such as Cu, or Al. However, the outer cover layer 115 may also include a non-metal such as a plastic. In addition, the outer cover layer 115 may include a non-metal such as a plastic, and a metal only on an outer surface thereof.

When the microwave probe 100f is coupled to the viewport 220b of the chamber 200a, the outer cover layer 115 is inserted into the groove G of the viewport 220b to be firmly secured therein. Since the outer cover layer 115 is secured to the groove G, trembling, vibration, deformation, or the like of the head 120b and the body 110 can be suppressed. In addition, if the outer cover layer 115 includes a metal, the body 110 and the outer cover layer 115 may form a coaxial cable-like structure, and thus contribute to improved signal transfer properties of the microwave probe 100f.

Figure 13A:
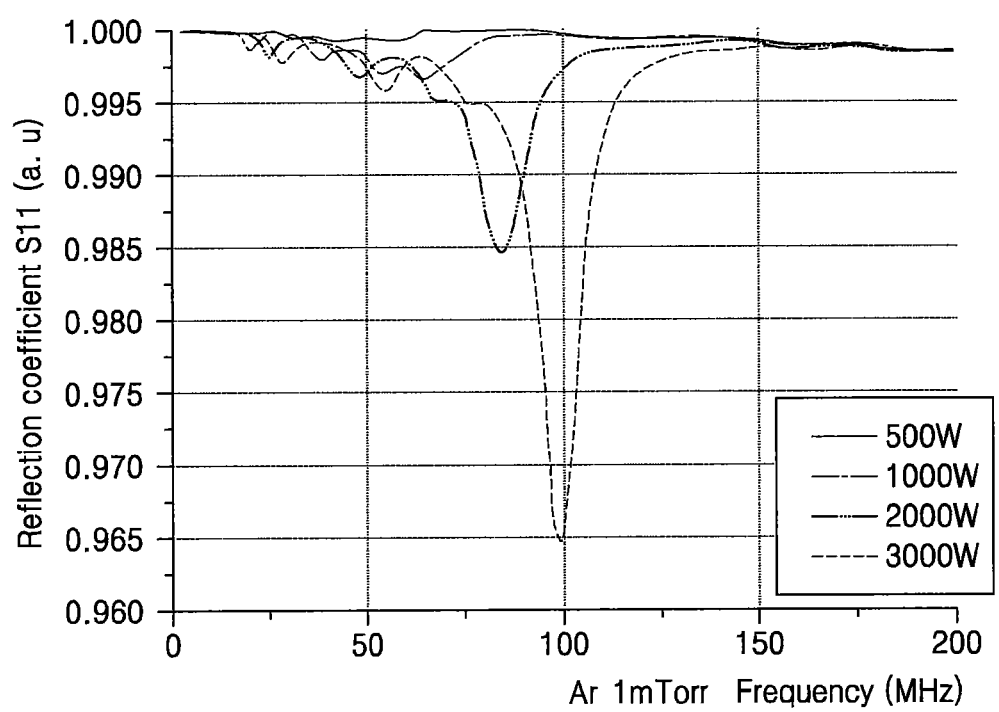
FIGS. 13A and 13B are graphs depicting reflection coefficients along with frequencies while a pressure and applied power inside a chamber are changed, using a microwave probe according to an example embodiment of the inventive concept.
Figure 13B:
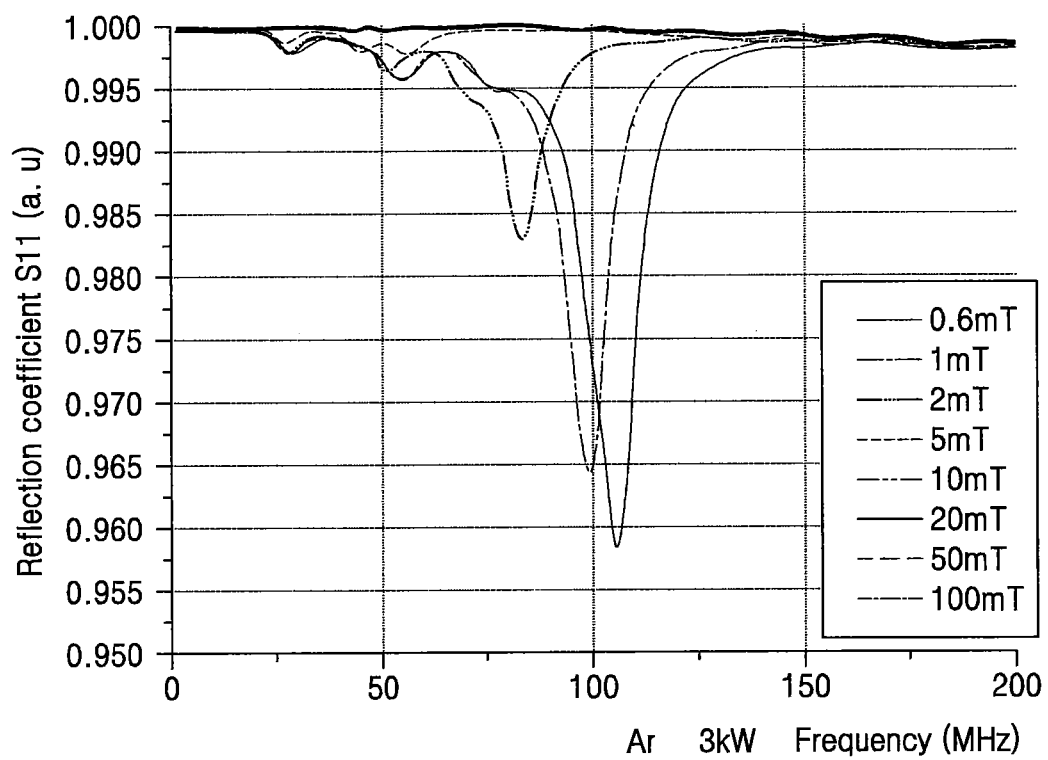

FIGS. 13A and 13B are graphs depicting reflection coefficients along with frequencies while a pressure and applied power inside a chamber are changed, using a microwave probe according to an example embodiment of the inventive concept. An x axis represents a frequency, and a y axis represents a reflection coefficient S11. FIG. 13A is a graph obtained by changing the applied power while a pressure of argon (Ar) gas inside the chamber is fixed at 1 mTorr, and FIG. 13B is a graph obtained by changing the pressure of Ar gas while the applied power is fixed at 3 kW.

Referring to FIG. 13A, it can be seen that a peak value of the reflection coefficient S11 increases with increasing applied power. That is, it can be seen that a resonant frequency increases with increasing power. The increase of the resonant frequency may mean an increase of a oscillation frequency ($f_{pe}$) of plasma, and the increase of the oscillation frequency ($f_{pe}$) of the plasma may finally mean an increase of an electron density of the plasma. Thus, it can be seen that the electron density of the plasma increases with increasing power. The reason for this may be that since energy, which is transferred to process gases, for example, Ar gas in the chamber, increases with increasing applied RF power, kinetic energy and collision frequency of the process gases increase, thereby increasing a possibility of plasma generation. As described above, it can be confirmed that since frequencies other than the resonant frequency are almost fully reflected, the reflection coefficient S11 is close to 1.

Referring to FIG. 13B, it can be seen that the peak value of the reflection coefficient S11 increases with increasing pressure in the chamber. That is, it can be seen that the resonant frequency increases with increasing pressure.

Like the above conclusion that the increase of the resonant frequency due to the increase of the power leads to the increase of the electron density of the plasma, the increase of the resonant frequency due to the increase of the pressure may also lead to the increase of the electron density of the plasma. The increase of the electron density of the plasma due to the increase of the pressure may be caused by the fact that since the increase of the pressure leads to an increase of an amount of the process gases, for example, Ar gas in the chamber, the collision frequency of the process gases increase, thereby increasing a possibility of plasma generation.

Figure 14:
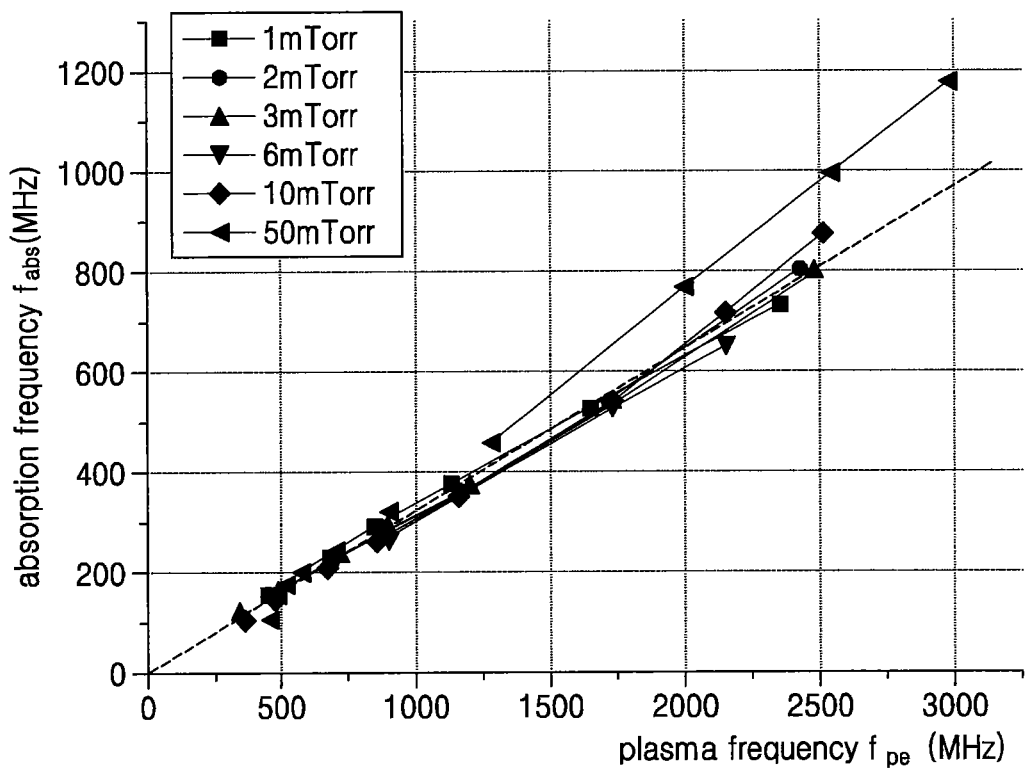
FIG. 14 is a graph depicting a correlation between an oscillation frequency of plasma and an absorption frequency of a surface wave depending upon a pressure change.

FIG. 14 is a graph depicting a correlation between an oscillation frequency of plasma and an absorption frequency of a surface wave depending upon a pressure change. An x axis represents the oscillation frequency ($f_{pe}$) of the plasma, and a y axis represents the absorption frequency ($f_{abs}$) of the surface wave, that is, a resonant frequency of the surface wave. Measurement may be performed in a chamber, on which a round viewport is mounted, under Ar discharge.

Referring to FIG. 14, it can be seen that, for each pressure, there is an approximate one dimensional graph relation (e.g., an approximate linear relation) between the oscillation frequency ($f_{pe}$) of the plasma and the absorption frequency ($f_{abs}$) of the surface wave. Thus, a value of the proportional factor k of Equation (3) may be found based on the graph of the relation between the oscillation frequency ($f_{pe}$) of the plasma and the absorption frequency ($f_{abs}$) of the surface wave. As described above, if the value of the proportional factor k is found and the resonant frequency is detected, an electron density of the plasma can be calculated.

Figure 15:
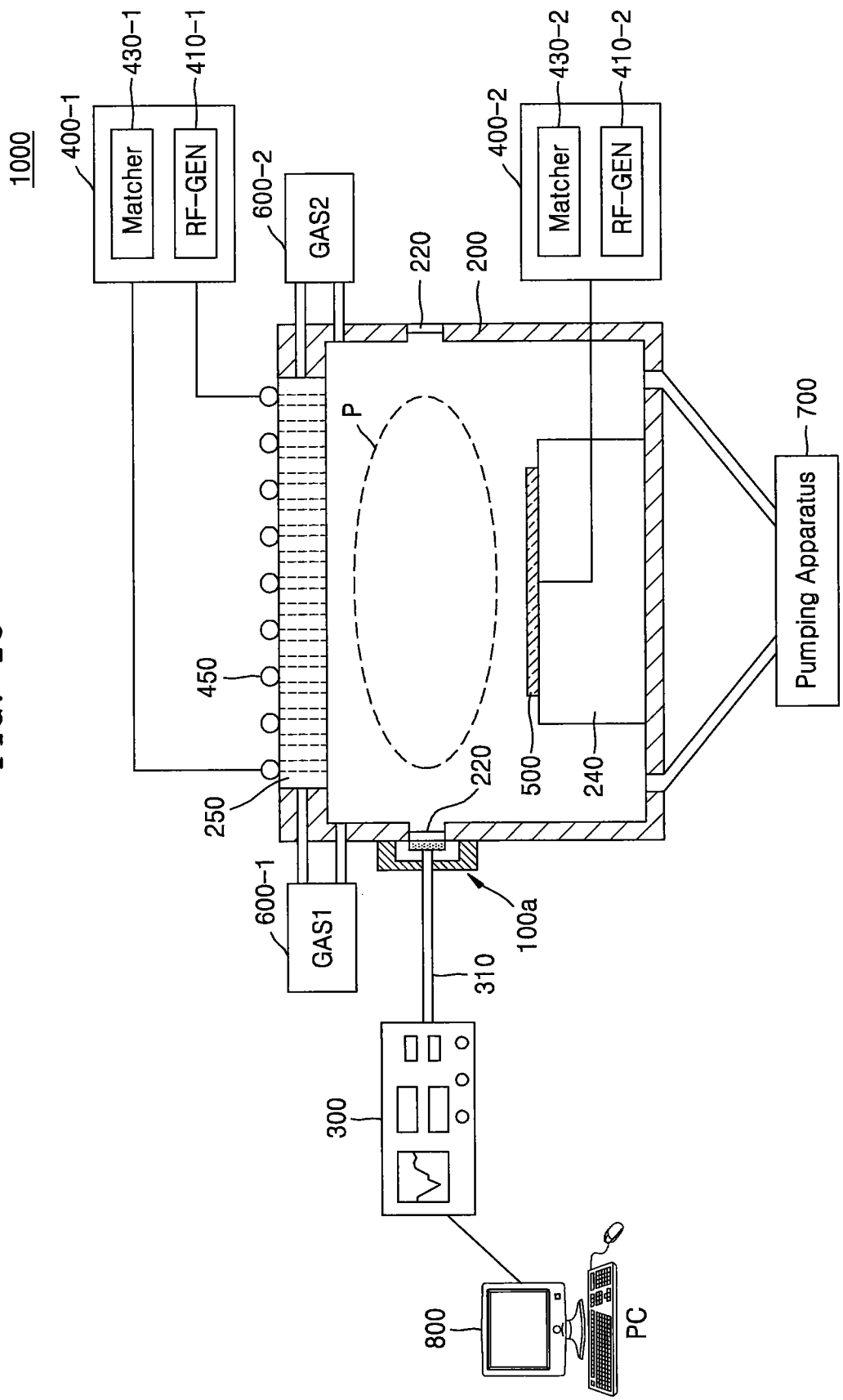
FIG. 15 is a schematic configuration diagram of a plasma monitoring system including a microwave probe according to an example embodiment of the inventive concept.

FIG. 15 is a schematic configuration diagram of a plasma monitoring system including a microwave probe according to an example embodiment of the inventive concept. In the interest of brevity, details which have been described above with reference to FIGS. 1A to 12B may be only briefly described or omitted.

Referring to FIG. 15, a plasma monitoring system 1000 according to the present example embodiment may include a microwave probe 100a, a chamber 200, a network analyzer 300, RF power supplies 400-1, 400-2, gas supplying sources 600-1, 600-2, a pumping device 700, and a computer 800 for analysis.

For example, the microwave probe 100a may be the microwave probe 100a of FIG. 2A. Of course, instead of the microwave probe 100a of FIG. 2A, any one of the microwave probes 100, 100b, 100c, 100d, 100e, 100f according to the other example embodiments may be used for the plasma monitoring system 1000 according to the present example embodiment. A structure of the microwave probe may variously changed in consideration of a shape of a viewport 220 of the chamber, or improvement in efficiencies of microwave application and/or signal reception. In addition, considering that a head can greatly contribute to improvement in efficiencies of microwave application and/or signal reception, the head may have various shapes as well as may include various-shaped patterns on a surface thereof, which is brought into contact with the viewport 220 as described above with reference to FIG. 5.

The chamber 200 may be a chamber for a plasma process. For example, as shown in FIG. 15, the chamber 200 may be a chamber for inductively coupled plasma (ICP). Of course, the chamber 200 is not limited to the chamber for ICP. For example, the plasma monitoring system 1000 according to the present example embodiment may employ various chambers such as a chamber for capacitively coupled plasma (CCP), a chamber for electron cyclotron resonance (ECR) plasma, a chamber for surface wave plasma (SWP), a chamber for helicon wave plasma, a chamber for e-beam plasma, and the like. The chamber and peripheral devices may also be collectively referred to as a plasma system, and the peripheral devices may slightly vary with a kind of chamber. For example, in the plasma monitoring system 1000 according to the present example embodiment, the chamber 200 for ICP, the RF power supplies 400-1, 400-2, the gas supplying sources 600-1, 600-2, and the pumping device 700 may be configured for an ICP system.

For reference, plasma can be divided into low temperature plasma and thermal plasma according to temperatures. Low temperature plasma is mainly used for semiconductor processes such as semiconductor fabrication, metal and ceramic thin film fabrication, material synthesis, and the like, and thermal plasma is used for metal cutting, and the like. Low temperature plasma can be divided again into atmospheric pressure plasma, vacuum plasma, next generation plasma, and the like according to applications. An atmospheric pressure plasma technique refers to a technique of generating low temperature plasma while a pressure of a gas is maintained at 100 Torr to atmospheric pressure (760 Torr), and may be used for surface modification, display flat panel cleaning, light sources for LCDs, and the like. A vacuum plasma technique refers to a technique of generating low temperature plasma while a pressure of a gas is maintained at 100 Torr or less, and may be used for dry etching, thin film deposition, PR ashing, ALD growth, and the like in semiconductor processes, and used for etching, thin film deposition, and the like with respect to a display flat panel in display processes. A next generation plasma technique may refer to a technique of generating advanced concept low temperature plasma and/or generating low temperature plasma capable of being used for next generation new technologies.

The chamber 200 may fundamentally include the wall 210, the viewport 220, the electrostatic chuck (ESC) 240, and a shower head 250. Since the wall 210 and the viewport 220 have been described above with respect to FIGS. 8A and 8B, details thereof will not be repeated in the interest of brevity. The electrostatic chuck 240 is arranged in a lower portion inside the chamber 200, and a wafer 500 may be placed on an upper surface of the electrostatic chuck 240 and secured thereto. The electrostatic chuck 240 may allow the wafer 500 to be secured thereto using electrostatic force. The shower head 250 is arranged in an upper portion inside the chamber 200, and may spray a process gas or the like into the chamber 200 through a plurality of spray holes.

The RF power supplies 400-1, 400-2 may include an upper RF power supply 400-1 and a lower RF power supply 400-2. The upper RF power supply 400-1 may include an RF generator 410-1, a matcher 430-1, and a coil 450. The RF generator 410-1 generates RF power, and the matcher 430-1 stabilizes plasma by adjusting impedance. The matcher 430-1 is also referred to as a matching box. The coil 450 is spirally arranged on an upper side of the chamber 200, and generates a magnetic field inside the chamber by RF power application. The magnetic field accelerates electrons or ions inside the chamber to further accelerate plasma generation.

The lower RF power supply 400-2 may also include an RF generator 410-2 and a matcher 430-2, and apply RF power to the wafer 500 instead of the coil. In some cases, RF power may be applied to the wafer 500 via the electrostatic chuck 240.

The gas supplying sources 600-1, 600-2 supply process gases required for a plasma process. Here, the process gases may refer to all gases, such as a source gas, a reaction gas, a purge gas, and the like, required for a corresponding plasma process. Although the two gas supplying sources 600-1, 600-2 are shown in FIG. 15, two or more gas supplying sources may be included according to the kinds of process gases. The process gases of the gas supplying sources 600-1, 600-2 are supplied to the shower head 250 through gas supplying tubes, and sprayed into the chamber 200 through the shower head 250. In some cases, a specific process gas of the gas supplying sources 600-1, 600-2 may be directly supplied into the chamber 200 through a gas supplying tube directly connected into the chamber 200.

The pumping device 700 may discharge gases inside the chamber 200 to the outside of the chamber 200 through a vacuum pump or the like after a plasma process. In addition, the pumping device 700 may serve to adjust a pressure inside the chamber 200.

The network analyzer 300 is as described above with reference to FIG. 11. The computer 800 for analysis may be a general personal computer (PC), a workstation, a supercomputer, or the like. An analysis program, which can calculate an electron density of plasma based on Equations (1) to (3), the proportional factor k, and the like, is installed in the computer 800 for analysis. Thus, the computer 800 for analysis may receive a detected resonant frequency that is input from the network analyzer 300, and calculate an electron density of plasma using the analysis program. In addition, the computer 800 for analysis may determine whether there is a problem in a plasma state by comparing the calculated electron density of the plasma with a pre-set reference value. Further, when there is a problem in the plasma state, the computer 800 for analysis may also analyze a cause thereof and suggest new process conditions for a plasma process in question.

The plasma monitoring system 1000 according to the present example embodiment includes the microwave probe 100*a* which is non-invasively coupled to the viewport 220 of the chamber 200, whereby the microwave probe 100*a* does not affect the plasma state inside the chamber 200. Thus, the plasma monitoring system 1000 can precisely detect the plasma state inside the chamber 200 using the microwave probe 100*a* and the network analyzer 300. In addition, the plasma monitoring system 1000 includes the microwave probe 100*a* which includes the body 110 including the insulation covering layer 114, the disk-shaped head 120, and the ground cover 140 covering the body 110 and the head 120 and maintaining a grounded state, thereby optimizing and maximizing microwave application and a measurement sensitivity to signals inside the chamber 200. Thus, the plasma monitoring system 1000 accurately detects the resonant frequency, and accurately calculates the electron density of the plasma based on the detected resonant frequency, thereby precisely monitoring whether there is a problem in the plasma state inside the chamber 200.

As described with reference to FIGS. 16 to 19, the plasma monitoring system 1000 according to the present example embodiment is used for determination of a time point of plasma stabilization, tool matching between chambers, determination of a time point of preventive maintenance (PM) for a chamber, sensing of in-process issues, and the like, thereby significantly contributing to optimization of a plasma process.

Figure 16:
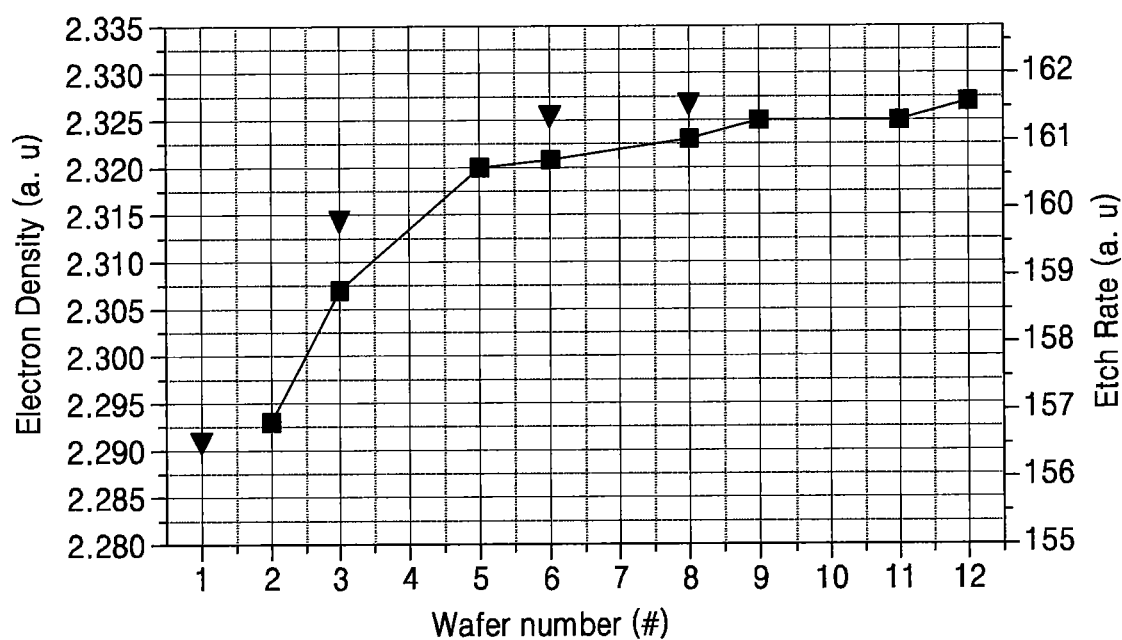
FIG. 16 is a graph showing a concept for determining a time point of stabilization of plasma inside a chamber using a plasma monitoring system according to an example embodiment of the inventive concept.

FIG. 16 is a graph showing a concept for determining a time point of stabilization of plasma inside a chamber using a plasma monitoring system according to an example embodiment of the inventive concept. An x axis represents a wafer number introduced into a chamber, a left y axis represents an electron density of plasma inside the chamber, and a right y axis represents an etch rate. The electron density of the plasma is marked by a symbol ■, and the etch rate is marked by a symbol ▼.

Referring to FIG. 16, when a plasma process is newly performed in the chamber (see the reference numeral 200 in FIG. 15) in an idle state, it is necessary to determine whether generated plasma reaches an appropriate state required for the plasma process in question. That is, before a wafer for devices is subjected to the plasma process, it is necessary to determine a time point of plasma stabilization, that is, a time point of plasma back-up, and only after the time point of plasma stabilization, the wafer for devices can be subjected to the plasma process.

Generally, dummy wafers are introduced into the chamber and subjected to a plasma process, followed by examining the dummy wafers, for example, etch rates for the dummy wafers, thereby determining whether plasma reaches an appropriate state. As such, in the existing method of determining the time point of plasma stabilization, a large number of dummy wafers, for example, one hundred or more dummy wafers may be consumed, and a lot of time may be spent since the dummy wafers need to be examined after the plasma process.

However, if the plasma monitoring system (1000 in FIG. 15) according to the present example embodiment is used, since the plasma state can be detected in real time, upon determining the time point of stabilization of plasma inside the chamber, consumption of the dummy wafer can be significantly reduced, and relatively short time can be spent. For example, the time point of plasma stabilization can be accurately determined with consumption of a few dummy wafers to dozens of dummy wafers.

As can be seen from the graph of FIG. 16, in the plasma process for each of the dummy wafers, the electron density of the plasma can be detected in real time using the plasma monitoring system (1000 in FIG. 15) according to the present example embodiment. As such, the electron density of the plasma is detected in real time, whereby since the plasma state inside the chamber can be somewhat predicted, examination of etch rates for a large number of dummy wafers may not be needed. For example, it may be sufficient only to examine etch rates for a few dummy wafers. Here, examination of the dummy wafers may correspond to confirming accuracy of the detected electron density of the plasma.

Figure 17:
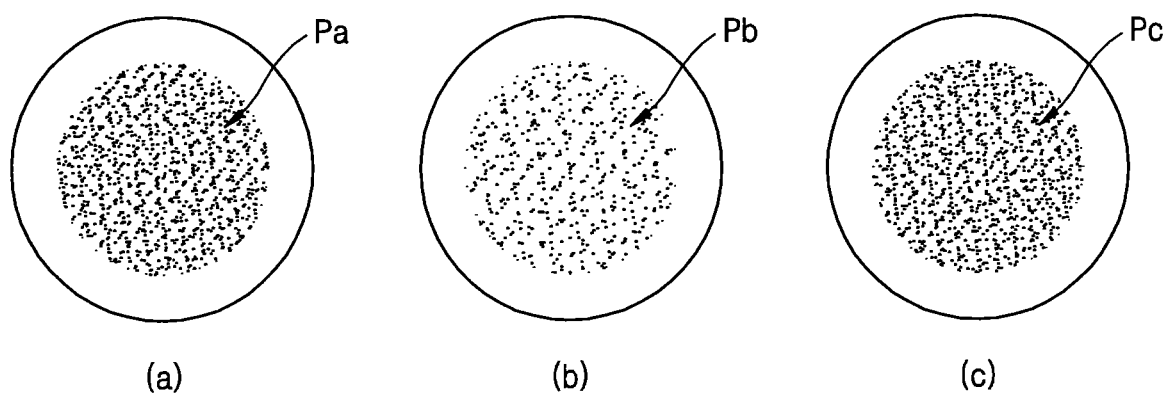
FIG. 17 is a conceptual diagram for explaining utilization of a plasma monitoring system according to an example embodiment of the inventive concept relating to tool matching between chambers.

FIG. 17 is a conceptual diagram for explaining utilization of a plasma monitoring system according to an example embodiment of the inventive concept in tool matching between chambers.

Referring to FIG. 17, even though plasma processes are performed in the same (a), (b), and (c) chambers under the same conditions, states of plasma inside chambers may be different, as shown in FIG. 17. For example, an electron density of plasma Pa of the (a) chamber may be 10, an electron density of plasma Pb of the (b) chamber may be 9, and an electron density of plasma Pc of the (c) chamber may be 10. These differences may be caused by, for example, wall conditions of the chambers.

Therefore, the wall conditions of the chambers may be found by monitoring the electron density of the plasma inside each of the chambers in real time using the plasma monitoring system according to the present example embodiment, thereby utilizing the plasma monitoring system in tool matching for an appropriate plasma process of each chamber.

Figure 18:
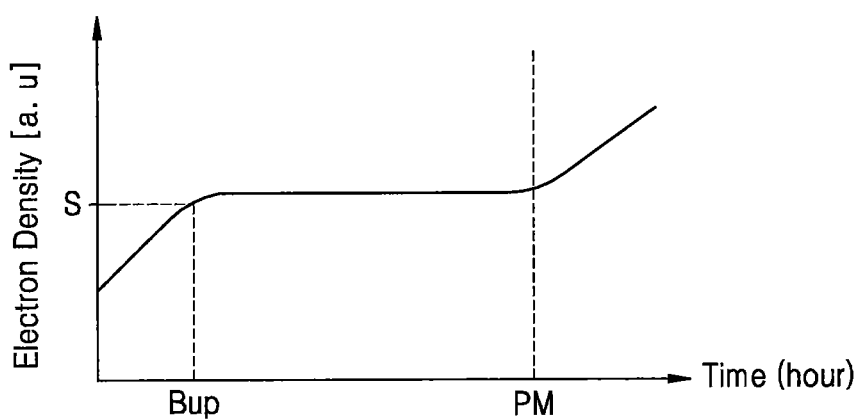
FIG. 18 is a graph showing a concept for determining a time point of preventive maintenance (PM) of a chamber using a plasma monitoring system according to an example embodiment of the inventive concept.

FIG. 18 is a graph showing a concept for determining a time point of PM of a chamber using a plasma monitoring system according to an example embodiment of the inventive concept.

Referring to FIG. 18, if a plasma process is performed in a chamber for a long period of time, a plasma state inside the chamber deviates from an appropriate plasma state. That is, as shown in FIG. 18, an electron density of the plasma starts to exceed an appropriate level after the time point of PM. Thus, if the time point of PM is reached, PM, such as cleaning and the like, for the chamber should be performed.

The plasma monitoring system according to the present example embodiment (1000 in FIG. 15) monitors the electron density of the plasma inside the chamber in real time, thereby relatively accurately determining the time point of PM. Thus, the plasma monitoring system can contribute to improvement in a plasma process efficiency due to reduction of a PM cycle and maintenance of a good chamber state.

For reference, a symbol Bup on an x axis may refer to the time point of plasma stabilization, that is, the time point of plasma back-up as described above with reference to FIG.

16, and a symbol S on a y axis may refer to the appropriate electron density of the plasma.

Figure 19:
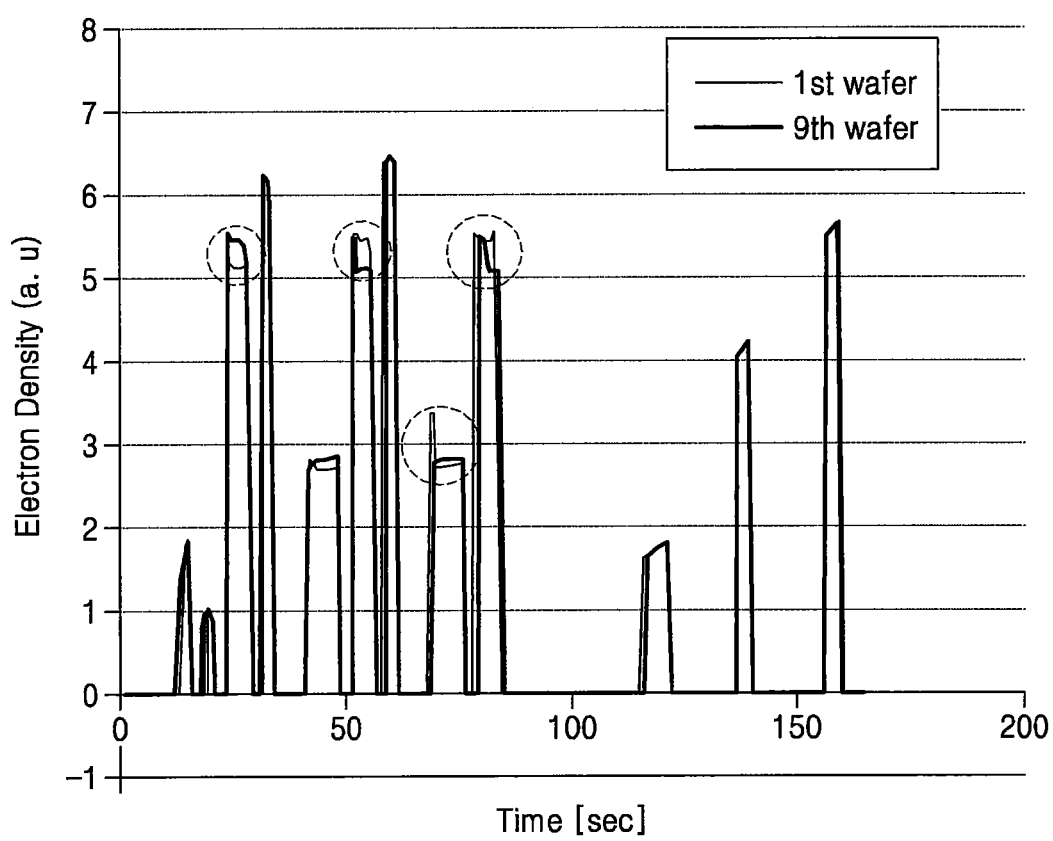
FIG. 19 is a graph depicting electron densities of plasma detected using a plasma monitoring system according to an example embodiment of the inventive concept in plasma processes for a first wafer and a ninth wafer.

FIG. 19 is a graph depicting electron densities of plasma detected using a plasma monitoring system according to an example embodiment of the inventive concept in plasma processes for a first wafer and a ninth wafer.

Referring to FIG. 19, a plasma process for one wafer may generally include a plurality of sub-plasma processes. As shown in FIG. 19, each of the plasma processes for the first wafer (thin line) and the ninth wafer (thick line) may include a plurality of sub-plasma processes. In addition, each of the sub-plasma processes may have a corresponding electron density of plasma, ranges on an x axis, in which the electron density is 0; these may be periods of time in which the plasma process is stopped for a short time.

The plasma processes for the first wafer and the ninth wafer may be performed in the same chamber under the same process conditions. Thus, the plasma electron densities of the sub-plasma processes for the first wafer and the ninth wafer should be the same. However, as shown in FIG. 19, it can be confirmed that the plasma electron densities in the sub-plasma processes are different. Thus, it can be seen that a problem occurred in the plasma process for the ninth wafer. More precisely, it can be seen that, among the sub-plasma processes, problems occurred in the sub-plasma processes (marked by dashed circles) showing noticeable differences in plasma electron densities. For reference, since plasma electron densities of second to eighth wafers were substantially the same as the plasma electron density of the first wafer, it can be anticipated that there was not a problem until or after the plasma process for the eighth wafer.

As such, the plasma monitoring system (1000 in FIG. 15) according to the present example embodiment measures the electron density of the plasma in the plasma process for each wafer in real time, thereby monitoring problems during the plasma process, that is, in-process issues in real time. In addition, when the in-process issues are discovered, causes thereof are analyzed and utilized, whereby the plasma monitoring system can contribute to optimization of the plasma process. Here, analysis and utilization of the causes may include, for example, removal of the discovered causes, solving the problems by changing process conditions when the causes cannot be removed, or the like.

Figure 20:
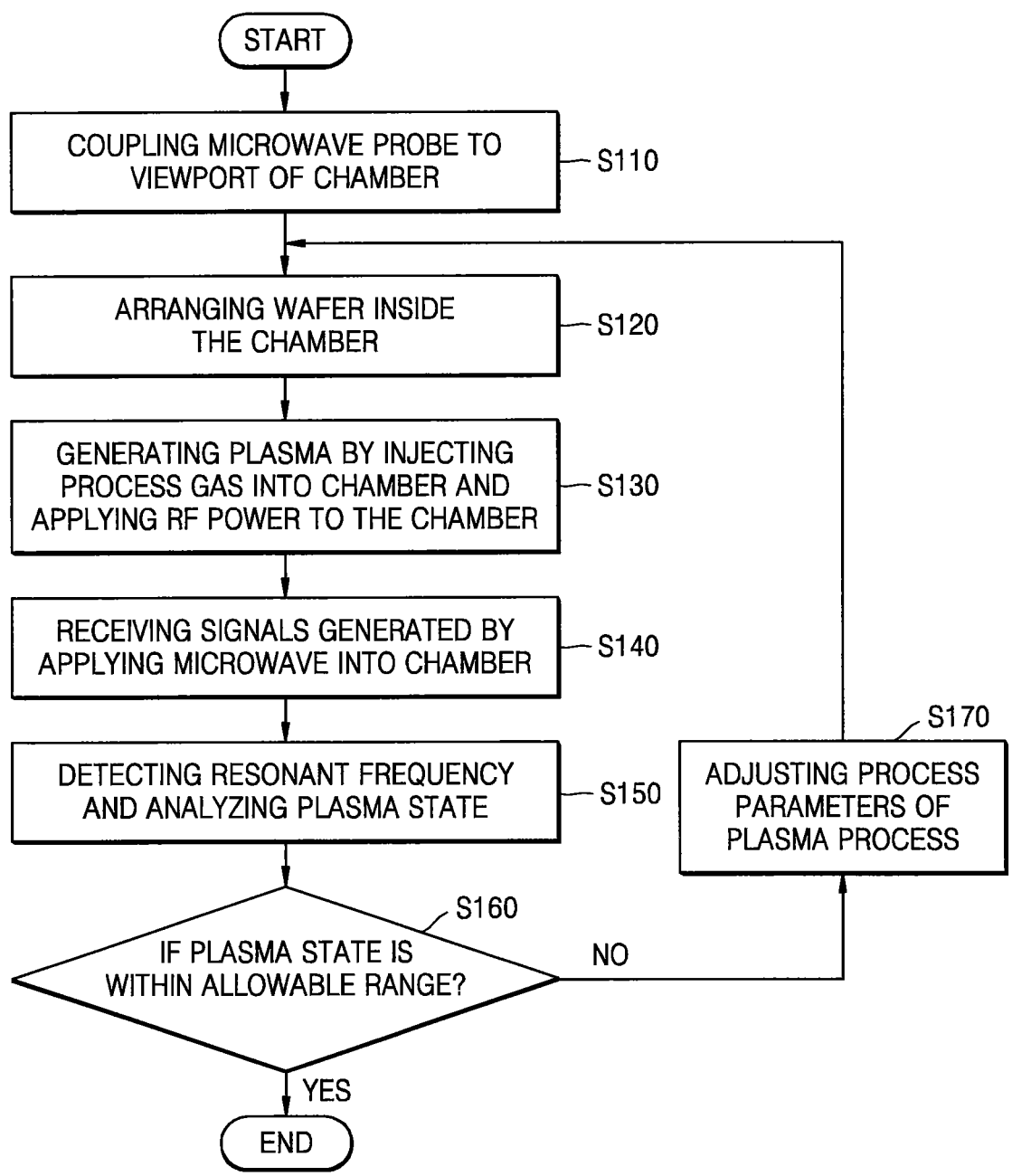
FIG. 20 is a flow chart illustrating a process of monitoring a plasma state and controlling a plasma process according to an example embodiment of the inventive concept.

FIG. 20 is a flow chart showing a process of monitoring a plasma state and controlling a plasma process according to an example embodiment of the inventive concept. For convenience, descriptions will be made with reference to FIG. 15 together.

Referring to FIG. 20, first, the microwave probe is coupled to the viewport 220 of the chamber 200 (S110). The microwave probe may be the microwave probe 100a of FIG. 2A. Of course, instead of the microwave probe 100a of FIG. 2A, the microwave probes 100, 100b to 100c according to the other example embodiments may be coupled to the viewport 220. In addition, when the viewport 220 has the structure illustrated in FIG. 12A, the microwave probe 100d, 100e, or 100f of FIG. 7A, 7B, or 12B may be coupled to the viewport 220. Coupling the microwave probe 100a to the viewport 220 may mean that the network analyzer 300 is also coupled to the viewport 220 through the microwave probe 100a. When the microwave probe 100a is coupled to the chamber 200, the computer 800 for analysis may be connected to the network analyzer 300, and thereby receive data for a resonant frequency transferred from the network analyzer 300 in real time. In addition, the computer 800 for analysis may not be connected to the network analyzer 300 until the network analyzer 300 detects the resonant frequency. After the network analyzer 300 detects the resonant frequency, the computer 800 for analysis may be connected to the network analyzer 300, and thereby receive the data for the resonant frequency, which is stored in the network analyzer 300.

The wafer 500 is arranged on the electrostatic chuck 240 inside the chamber 200 (S120). The wafer 500 may also be arranged on the electrostatic chuck 240 before the coupling of the microwave probe 100a.

Plasma is generated by injecting the process gases and applying RF power into the chamber 200 (S130). The process gases may be injected into the chamber 200 in such a manner that the process gases supplied from the gas supplying sources 600-1, 600-2 are sprayed through the shower head 250. The application of the RF power may be performed in such a manner that the RF power is respectively applied to the coil 450 on the upper side of the chamber 200 through the upper RF power supply 400-1 and to the wafer 500 inside the chamber 200 through the lower RF power supply 400-2.

In the present operation, the generation of the plasma may refer to performing a plasma process using the generated plasma. For example, the plasma process may include etching, deposition, diffusion, surface treatment, novel material synthesis processes, and the like.

Using the microwave probe 100a, a microwave is applied into the chamber 200, and signals generated inside the chamber 200 are received (S140). An absorption frequency signal of a surface wave, that is, a resonant frequency signal of the surface wave may be included in the generated signals. The microwave may be generated in the network analyzer 300 and applied into the chamber 200 through the microwave probe 100a. In addition, the signals generated inside the chamber 200 may be received through the microwave probe 100a, and transferred to the network analyzer 300 through the external wire 310.

A resonant frequency of the surface wave is detected from the received signals, and a plasma state is analyzed based on the resonant frequency (S150). The detection of the resonant frequency may be performed by the network analyzer 300. For example, the network analyzer 300 may detect the resonant frequency of the surface wave by detecting a peak value of a reflection coefficient S11.

The analysis of the plasma state may be performed by the computer 800 for analysis. For example, the computer 800 for analysis receives the detected resonant frequency that is input from the network analyzer 300, and calculates an electron density of the plasma using an analysis program. The analysis program may be a program for calculating the electron density of the plasma using Equations (1) to (3), the value of the proportional factor k, and the like.

Whether the plasma state is within an allowable range is determined (S160). The determination of whether the plasma state is within the allowable range may be performed by the computer 800 for analysis. For example, whether there is a problem in the plasma state may also be determined by comparing the calculated plasma electron density with a pre-set reference value. Further, when there is a problem in the plasma state, the computer 800 for analysis may also analyze a cause thereof and suggest new process conditions for the plasma process in question.

If the plasma state is within the allowable range (Yes), monitoring of the plasma state is terminated. If the plasma state is outside of the allowable range (No), process parameters of the plasma process are adjusted (S170). The adjustment of the process parameters may be performed through, for example, increase or decrease in pressures of the process gases, increase or decrease in applied RF power, or the like. The adjustment of the process parameters may be performed based on data obtained through a simulation in the computer 800 for analysis.

After the adjustment of the process parameters, the process returns to arranging a new wafer inside the chamber (S120), and the plasma process and monitoring thereof are performed again.

Since the method of monitoring the plasma state according to the present example embodiment is performed using the microwave probe, which is non-invasively coupled to the chamber 200 and has the structure illustrated in any one of FIG. 1A to FIG. 12B, the plasma state inside the chamber 200 can be precisely detected and monitored by the method due to a high reception sensitivity to the signals inside the chamber 200, with no influence on the plasma state inside the chamber 200. In addition, the method of controlling the plasma process according to the present example embodiment appropriately controls process conditions of the plasma process based on accurate monitoring of the plasma state inside the chamber 200 using the microwave probe, thereby optimizing the plasma process.

Figure 21:
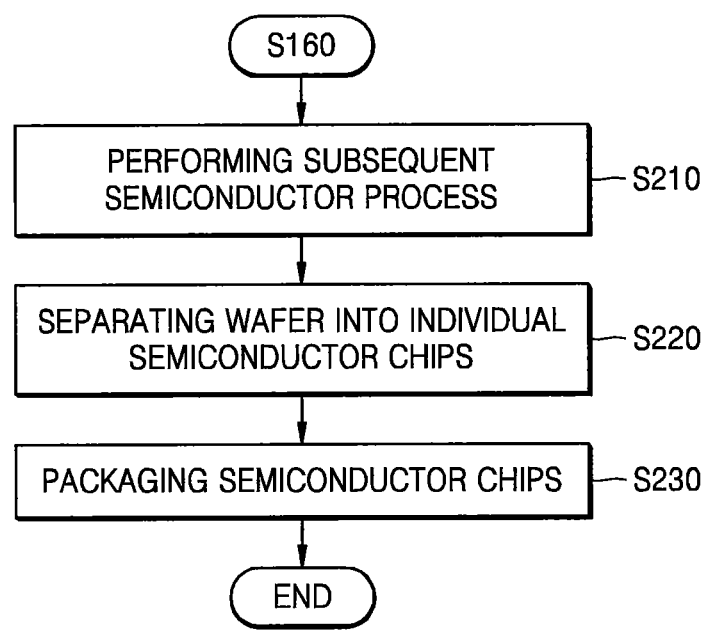
FIG. 21 is a flow chart illustrating a process of fabricating a semiconductor device through control of a plasma process according to an example embodiment of the inventive concept.

FIG. 21 is a flow chart showing a process of fabricating a semiconductor device through the control of the plasma process according to an example embodiment of the inventive concept. In the interest of brevity, details which have been described above with reference to FIG. 20 may be only briefly described or omitted.

Referring to FIG. 21, first, the methods of monitoring the plasma state and controlling the plasma process described above with reference to FIG. 20 are performed. The methods of monitoring the plasma state and controlling the plasma process may include a plasma process for the wafer 500. For example, the generating of the plasma (S130) as described with reference to FIG. 20 may correspond to the plasma process for the wafer 500.

For reference, in FIG. 21, operation "S160" may refer to performing the methods of monitoring the plasma state and controlling the plasma process as described with reference to FIG. 20, and an arrow from operation "S160" may mean that the process proceeds to the next operation since the methods of monitoring the plasma state and controlling the plasma process are completed. More precisely, in operation S160 of determining the allowable range of the plasma state in FIG. 20, the arrow from operation "S160" may mean that since the plasma state is within the allowable range (Yes), the methods of monitoring the plasma state and controlling the plasma process are completed, and the process proceeds to the next operation.

A subsequent semiconductor process for the wafer 500 is performed (S210). The subsequent semiconductor process for the wafer 500 may include various processes. For example, the subsequent semiconductor process for the wafer 500 may include a deposition process, an etching process, an ion process, a cleaning process, and the like. The deposition process, the etching process, the ion process, the cleaning process, and the like may be processes using plasma, or may be processes not using plasma. If the processes set forth above are processes using plasma, the methods of monitoring the plasma state and controlling the plasma process described above may be used again. The subsequent semiconductor process for the wafer 500 is performed, thereby forming integrated circuits and wires required for a semiconductor device in question. The subsequent semiconductor process for the wafer may also include a process of testing a wafer-level semiconductor device.

The wafer 500 is separated into individual semiconductor chips (S220). The separation into the individual semiconductor chips may be performed through a sawing process using a blade or laser.

Next, a packaging process for the semiconductor chips is performed (S230). The packaging process may refer to mounting the semiconductor chips on a PCB and sealing the chips with a sealant. The packaging process may include forming a stack package by stacking a plurality of semiconductors as multiple layers on the PCB, or forming a package on package (POP) structure by stacking a stack package on another stack package. A semiconductor device or a semiconductor package may be completed through the packaging process for the semiconductor chips. After the packaging process, a test process for the semiconductor package may be performed.

The method of fabricating a semiconductor device according to the present example embodiment performs plasma state monitoring and plasma process control using the plasma monitoring system 1000 of FIG. 15, thereby optimizing the plasma process. In addition, the method of fabricating a semiconductor device fabricates semiconductor devices based on the optimized plasma process, thereby realizing excellent and highly reliable semiconductor devices.

While the inventive concept has been particularly shown and described with reference to example embodiments thereof, it will be understood that various changes in form and details may be made therein without departing from the spirit and scope of the following claims.

What is claimed is:

1. A plasma monitoring system comprising:
a chamber for a plasma process;
an RF power supply for generating plasma inside the chamber;
a viewport on the chamber;
a microwave probe configured to be non-invasively coupled to the viewport on the chamber, the microwave probe comprising a body and a head at a first end of the body; and
a network analyzer outside the chamber and configured to be electrically connected to the microwave probe,
wherein the head comprises a flat plate connected to the first end of the body,
when the microwave probe is coupled to the viewport, a surface of the head contacts an exposed outer surface of the viewport,
when the microwave probe is coupled to the viewport, the microwave probe is configured to apply a microwave generated by the network analyzer into the chamber through the head and to receive signals generated inside the chamber through the head in the plasma process without an influence on a plasma state inside the chamber, and
the network analyzer is configured to detect a resonant frequency based on the received signals.

2. The plasma monitoring system according to claim 1, wherein the body extends in one direction,
when the microwave probe is coupled to the viewport, the surface of the head contacts the outer surface of the viewport without causing a change in shape of the viewport.

3. The plasma monitoring system according to claim 1, further comprising a computer connected to the network analyzer, wherein the computer is configured to analyze the plasma state inside the chamber using an analysis program based on the detected resonant frequency.

4. The plasma monitoring system according to claim 1, wherein the viewport has a flat plate shape and is held in a through-hole in a wall of the chamber, and
the head has an area that is substantially the same as or less than an area of a window region of the viewport through which light is transmitted.

5. The plasma monitoring system according to claim 1, wherein the microwave probe comprises a ground cover surrounding the body and the head, the ground cover comprising a base having a through-hole defined in a central portion thereof,
an outer rim of the ground cover that extends outwardly away from an outer periphery of the base is coupled to a wall of the chamber to be grounded when the microwave probe is coupled to the viewport,
the outer rim defines an opening in which the head is received, and
the body extends to the outside of the ground cover through the through-hole, the body being insulated from the ground cover by an insulating layer on an outer surface of the body.

6. The plasma monitoring system according to claim 1, wherein,
when the microwave probe is coupled to the chamber, the body is electrically connected to the network analyzer through a connector connected to a second, opposite end of the body.

7. The plasma monitoring system according to claim 1, wherein the head of the microwave probe comprises a circular flat plate.

8. The plasma monitoring system according to claim 7, wherein the head of the microwave probe comprises a plurality of concentric circular grooves on a surface of the circular flat plate.

9. The plasma monitoring system according to claim 1, wherein the body of the microwave probe comprises a flexible metal layer and an insulation covering layer covering the metal layer.

10. The plasma monitoring system according to claim 1, wherein the body of the microwave probe comprises a metal layer having a circular pillar shape and an insulation covering layer covering the metal layer.

11. The plasma monitoring system according to claim 1, wherein an outer surface of a wall of the chamber is in the same plane as the outer surface of the viewport.

12. The plasma monitoring system according to claim 1, wherein the microwave probe comprises a ground cover comprising a base having a through-hole defined therein through which the body extends and an outer rim that extends outwardly from the base and surrounds the head,
the outer rim defines an opening in which the head is received, and
the outer rim is coupled to a wall of the chamber when the microwave probe is coupled to the viewport.

13. The plasma monitoring system according to claim 12, wherein the outer rim of the ground cover contacts each of the outer surface of the viewport and an outer surface of the wall of the chamber when the microwave probe is coupled to the viewport.

14. The plasma monitoring system according to claim 12, wherein the outer rim of the ground cover is spaced apart from the head.

15. The plasma monitoring system according to claim 1, further comprising an insulating liner on an inner surface of a wall of the chamber.

16. A plasma monitoring system comprising:
a chamber for a plasma process;
an RF power supply for generating plasma inside the chamber;
a microwave probe configured to be non-invasively coupled to a viewport on the chamber, the microwave probe comprising a body and a head at an end of the body; and
a network analyzer outside the chamber and configured to be electrically connected to the microwave probe,
wherein, when the microwave probe is coupled to the viewport, the microwave probe is configured to apply a microwave generated by the network analyzer into the chamber through the head and to receive signals generated inside the chamber through the head in the plasma process without an influence on a plasma state inside the chamber, and
the network analyzer is configured to detect a resonant frequency based on the received signals.

17. The plasma monitoring system according to claim 16, further comprising a computer connected to the network analyzer,
wherein the computer is configured to analyze the plasma state inside the chamber using an analysis program based on the detected resonant frequency.

18. The plasma monitoring system according to claim 17, wherein the computer is configured to calculate an electron density of plasma inside the chamber based on the resonant frequency.

19. A plasma monitoring system comprising:
a chamber for a plasma process;
an RF power supply for generating plasma inside the chamber;
a viewport on the chamber;
a microwave probe configured to be non-invasively coupled to the viewport on the chamber, the microwave probe comprising:
a body;
a head at an end of the body; and
a ground cover comprising a base having a through-hole defined therein through which the body extends and an outer rim that extends outwardly from an outer periphery of the base and surrounds the head; and
a network analyzer outside the chamber and configured to be electrically connected to the microwave probe,
wherein the head comprises a flat plate connected to the end of the body,
when the microwave probe is coupled to the viewport, a surface of the head contacts an exposed outer surface of the viewport and the outer rim is coupled to a wall of the chamber,
when the microwave probe is coupled to the viewport, the microwave probe is configured to apply a microwave generated by the network analyzer into the chamber through the head and to receive signals generated inside the chamber through the head in the plasma process without an influence on a plasma state inside the chamber, and
the network analyzer is configured to detect a resonant frequency based on the received signals.

* * * * *